United States Patent [19]

Sher et al.

[11] Patent Number: 5,723,489

[45] Date of Patent: Mar. 3, 1998

[54] ARYLOXYPROPANOLAMINE BETA 3 ADRENERGIC AGONISTS

[75] Inventors: Philip M. Sher, Plainsboro; William N. Washburn, Titusville; Kathleen M. Poss, Lawrenceville, all of N.J.

[73] Assignee: Bristol-Myers Squibb Company, Princeton, N.J.

[21] Appl. No.: 646,164

[22] Filed: May 7, 1996

Related U.S. Application Data

[62] Division of Ser. No. 352,824, Dec. 2, 1994, Pat. No. 5,541,204.

[51] Int. Cl.⁶ .............. A61K 31/135; A61K 31/335; C07C 217/32; C07C 217/34
[52] U.S. Cl. .............. 514/466; 514/539; 514/524; 514/567; 514/605; 514/620; 514/648; 514/650; 514/652; 549/445; 558/422; 560/36; 560/42; 562/441; 562/451; 564/99; 564/165; 564/321; 564/337; 564/349; 564/350; 564/351
[58] Field of Search .............. 564/99, 165, 321, 564/337, 349, 350, 351; 562/441, 451; 560/36, 42; 558/422; 549/445; 514/466, 539, 524, 567, 605, 620, 648, 650, 652

[56] References Cited

U.S. PATENT DOCUMENTS

| | | | |
|---|---|---|---|
| 3,562,297 | 2/1971 | Howe et al. | 260/347 |
| 3,634,511 | 1/1972 | Howe et al. | 260/562 |
| 3,655,661 | 4/1972 | Wasson | 544/134 |
| 3,712,927 | 1/1973 | Howe et al. | 260/471 |
| 3,812,125 | 5/1974 | Wasson | 544/367 |
| 3,906,110 | 9/1975 | Francis | 424/330 |
| 3,959,486 | 5/1976 | LeCount et al. | 424/324 |
| 4,110,472 | 8/1978 | Hiltmann et al. | 424/330 |
| 4,134,983 | 1/1979 | Baldwin | 514/326 |
| 4,210,753 | 7/1980 | Tominaga et al. | 544/128 |
| 4,289,883 | 9/1981 | Tominaga et al. | 546/158 |
| 4,302,588 | 11/1981 | Tominaga et al. | 546/158 |
| 4,338,330 | 7/1982 | Gillet et al. | 424/273 |
| 4,338,333 | 7/1982 | Ainsworth et al. | 424/309 |
| 4,374,840 | 2/1983 | Shiratsuchi et al. | 424/263 |
| 4,479,949 | 10/1984 | Iwao et al. | 514/233.8 |
| 4,482,562 | 11/1984 | Shiratsuchi et al. | 424/263 |
| 4,552,969 | 11/1985 | Iwao et al. | 548/179 |
| 4,558,125 | 12/1985 | Iwao et al. | 544/135 |
| 4,707,497 | 11/1987 | Cecchi et al. | 514/647 |
| 4,772,631 | 9/1988 | Holloway et al. | 514/539 |
| 4,853,383 | 8/1989 | Baldwin et al. | 514/235.8 |
| 4,990,668 | 2/1991 | Mai et al. | 564/349 |
| 5,053,514 | 10/1991 | Fujioka et al. | 546/157 |
| 5,061,727 | 10/1991 | Bloom et al. | 514/465 |
| 5,198,448 | 3/1993 | Fujioka et al. | 514/312 |
| 5,254,595 | 10/1993 | Guzzi et al. | 548/306.4 |

FOREIGN PATENT DOCUMENTS

| | | |
|---|---|---|
| 883069 | 8/1980 | Belgium . |
| 0 023 385 | 2/1981 | European Pat. Off. . |
| 2254-324 | 8/1975 | France . |
| 2254478 | 5/1973 | Germany . |
| 4133145 | 4/1993 | Germany . |
| 49-4020-768 | 5/1974 | Japan . |
| 49-4048-428 | 12/1974 | Japan . |
| 50-5012-425 | 5/1975 | Japan . |
| 50-5012-426 | 5/1975 | Japan . |
| 50-5012-427 | 5/1975 | Japan . |
| 57-7024-375 | 2/1982 | Japan . |
| 7006354 | 11/1970 | Netherlands . |
| 444287 | 6/1977 | Spain . |

OTHER PUBLICATIONS

Petrov et al., Chemical Abstracts, Vo. 82, abstract 17546.

*Primary Examiner*—Richard L. Raymond
*Attorney, Agent, or Firm*—Burton Rodney

[57] ABSTRACT

Compounds of the formula

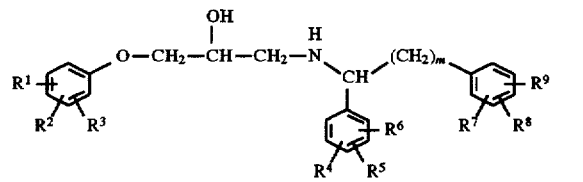

and pharmaceutically acceptable salts thereof wherein:

$R^1$ to $R^9$ are as defined herein and m is the integer 0 or 1. These compounds are beta 3 adrenergic receptor agonists and are useful, therefore for example, in the treatment of diabetes, obesity, gastrointestinal diseases and achalasia.

16 Claims, No Drawings

ARYLOXYPROPANOLAMINE BETA 3 ADRENERGIC AGONISTS

This is a division of application Ser. No. 08/352,824, filed Dec. 2, 1994 now U.S. Pat. No. 5,541,204.

BRIEF DESCRIPTION OF THE INVENTION

The present invention is directed to compounds of the formula

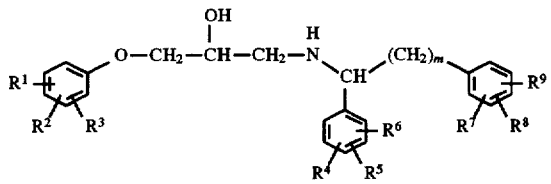

and pharmaceutically acceptable salts thereof. As used in formula I, and throughout the specification, the symbols have the following meanings:

$R^1$, $R^2$ and $R^3$ are independently hydrogen, hydroxy, alkoxy, nitro, amino, alkylsulfonylamino, acylamino, alkylsulfonyl, alkyl, cycloalkyl, phenyl, hydroxymethyl, cyano, aminocarbonyl, halogen or trifluoromethyl. In addition, two of the three substituents ($R^1$, $R^2$ and $R^3$) may together with the carbon atoms to which they are attached form a heterocycle.

$R^4$, $R^5$ and $R^6$ are independently hydrogen, alkoxycarbonyl, carboxy, aminocarbonyl, alkylaminocarbonyl, dialkylaminocarbonyl, alkoxycarbonylmethyl, carboxymethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl. In addition, two of the three substituents ($R^4$, $R^5$ and $R^6$) may together be methylenedioxy or benzo such that they together with the benzene ring to which they are attached form naphthyl;

$R^7$, $R^8$ and $R^9$ are independently hydrogen, alkoxycarbonyl, carboxy, aminocarbonyl, alkylaminocarbonyl, dialkylaminocarbonyl, alkoxycarbonylmethyl, carboxymethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl. In addition, two of the three substituents ($R^7$, $R^8$ and $R^9$) may together be methylenedioxy or benzo such that they together with the benzene ring to which they are attached form naphthyl; and m is the integer 0 or 1; provided that when $R^1$ is hydrogen, then $R^2$ and $R^3$ may not be halogen and alkyl, chloro and hydrogen, or acylamino and hydrogen.

Compounds of the formula I where the substituents are as defined above are novel compounds provided that: a) when m is zero and $R^4$ to $R^9$ are all hydrogen and two of the three substituents $R^1$, $R^2$ and $R^3$ together with the carbons to which they are attached form a heterocycle, the heterocycle must be other than a 2-hydroxypyridine or a 3,4-dihydro-2-hydroxy-pyridine; and b) when m is zero and $R^1$ and $R^4$ to $R^9$ are all hydrogen, then $R^2$ and $R^3$ may not be 1) hydrogen and hydroxymethyl, 2) alkyl and alkyl, 3) alkyl and alkoxy, 4) alkoxy and alkoxy, or 5) chloro and chloro.

The compounds of formula I possess activity at the beta 3 adrenergic receptor in mammals and are useful in the treatment of diabetes, obesity, gastrointestinal diseases and achalasia.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 12 carbon atoms, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "cycloalkyl" refers to saturated cyclic hydrocarbon groups containing 3 to 7 ring carbons.

The term "lower alkyl" as employed herein includes such alkyl groups as described above containing 1 to 6 carbon atoms.

The term "alkoxy" refers to any of the above alkyl groups linked to an oxygen atom.

The term "lower alkoxy" refers to any of the above lower alkyl groups linked to an oxygen atom.

The term "heterocycle" refers to 5- and 6-membered rings containing from 1 to 3 heteroatoms. The heterocycle may be aromatic or non-aromatic, and the heteroatoms may be oxygen, nitrogen, and sulfur. Examples of suitable heterocycles include furan, 2,3-dihydrofuran, pyrrole, 2,3-dihydropyrrole, thiophene, 2,3-dihydrothiophene, oxazole, imidazole, thiazole, 1,2,3-triazole, 1,2,3-thiadiazole, pyridine and pyrimidine. The heterocycle may be optionally substituted by one or more of the following groups: hydroxy, oxo, halogen, trifluoromethyl, cyano, amino, nitro, alkyl, alkylsulfonyl, and alkoxy. Examples of substituted heterocycles include 2-nitrofuran, 2-chloropyrrole, 3-cyanopyrrole, 2-(trifluoromethyl)thiophene, 2-methyloxazole, oxazol-2-one, imidazole-2-one, 2-aminothiazole, 2-methoxythiazole, N-methylsulfonyl-1,2,3-triazole, 2-hydroxypyridine, 3,4-dihydro-2-hydroxypyridine and uracil. Where these heterocycles are formed from two of the three substituents $R^1$, $R^2$ and $R^3$ and the carbon atoms to which they are attached, there may result more than one possible benzoheterocycle. All such isomers are contemplated. For example, the heterocycle pyridine may be incorporated in either a quinoline or an isoquinoline ring system.

The term "halogen" or "halo" refers to chlorine, bromine, fluorine or iodine.

The compounds of formula I can be converted to salts, in particular pharmaceutically acceptable salts using art recognized procedures. The compounds of formula I have a basic center, and they can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids, for example methane- or p-toluenesulfonic acid. Corresponding acid addition salts can also be formed having, if desired, an additionally present basic center. The compounds of formula I having at least one acid group can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form.

It should be understood that the present invention includes prodrug forms of the compounds of formula I.

The compounds of the instant invention may be in the free or hydrate form, and may be obtained by methods exemplified by the following descriptions.

Compounds of formula I may be prepared by coupling compounds of formula

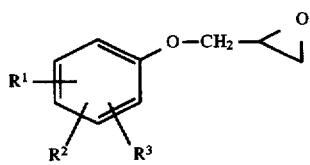

II with a compound of formula

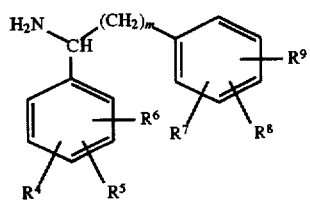

III by heating them together optionally in the presence of a solvent such as ethanol or by the method described in R. K. Atkins et al., Tet. Lett., 27, 2451 (1986).

Compounds of formula II are available in optically active form by reacting an activated glycidyl alcohol such as (2S)-(+)-glycidyl 3-nitrobenzenesulfonate with a phenoxide such as sodium phenoxide in an organic solvent such as dimethylformamide as described in J. M. Klunder et al., J. Org. Chem., 54, 1295 (1989).

It is recognized that the required phenol

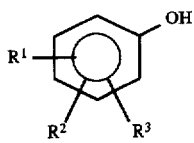

IIA may not always be readily available. In many cases such phenols may be prepared from the analogous benzaldehydes of formula

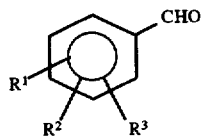

IIB or the acetophenones of formula

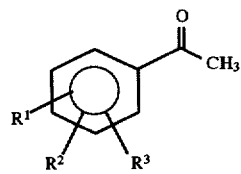

IIC by Baeyer-Villiger oxidation, for example with peracetic acid or m-chloroperoxybenzoic acid, followed by ester hydrolysis, for example with aqueous sodium hydroxide, or from the analogous aryl bromide of formula

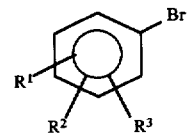

IID or the aryl iodide of formula

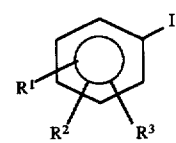

IIE by a variety of methods discussed in the series *Compendium of Organic Synthetic Methods* (John Wiley & Sons), Section 40.

The compounds of formula III may be prepared from any of three precursors, ketone IV, alcohol VI, or aldehydes VII or XI.

Compounds of formula III are prepared by fusion of a ketone of formula

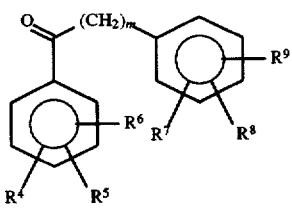

IV with ammonium formate followed by heating with a strong mineral acid such as a 37% aqueous hydrochloric acid-methanol mixture or hydrogen chloride (gas) in methanol solution.

Alternatively, compounds of formula III may be prepared by condensation of the compounds of formula IV with O-alkyl- or O-benzylhydroxylamines in a solvent such as a pyridine-ethanol mixture to form the oxime ethers of formula

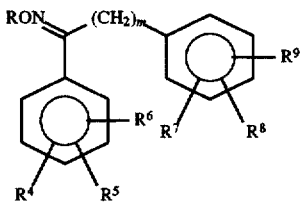

wherein R is alkyl or benzyl. Compounds of formula V may be converted to racemic amines of formula III by reduction with, for example, diborane. Optically active amines of formula III, where m is 1, are available by reduction of compounds of formula V with borane-norephedrine adducts as described in Y. Sakito et al., *Tet. Lett.*, 29, 223 (1988).

Additional methods for the preparation of compounds of formula III from the compounds of formula IV include:

1. Asymmetric reduction of the N-acyl hydrazone derivative of the ketones IV followed by reduction of the resultant N-acyl hydrazine to provide optically active amines of formula III where m is 1. These methods are described in M. J. Burk et al., *Tet.*, 50, 4399 (1994); and
2. Reductive amination of the ketones of formula IV with sodium cyanoborohydride and ammonia as described in C. F. Lane, *Synth.*, 135 (1975) to provide the compounds of formula III.

Compounds of formula III are also available from alcohols of formula

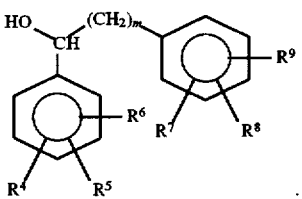

These alcohols may be tosylated or converted to the corresponding chloride or bromide by the methods discussed in the series *Compendium of Organic Synthetic Methods* (John Wiley & Sons), Section 138 and then convened to the compounds of formula III by treatment with ammonia in a solvent such as tetrahydrofuran or by sequential treatment with an azide source such as lithium azide in a solvent such as ethanol followed by a reducing agent such as triphenylphosphine.

Alternatively the alcohols of formula VI may be converted to the corresponding azides directly by treatment with diphenylphosphoryl azide and 1,8-diazabicyclo [5.4.0] undec-7-ene as described in A. S. Thompson et al., *J. Org. Chem.*, 58, 5886 (1993). Subsequent reduction, for example with triphenylphosphine then provides the compounds of formula III. Optically active compounds of formula III where m is 1 are available by this route when the corresponding alcohol starting materials are optically active.

The compounds of formula III are available in optically active fore by reacting aldehydes of formula

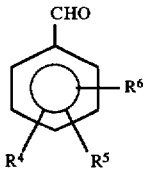

and optically active phenylglycinol to form the intermediate imines of formula

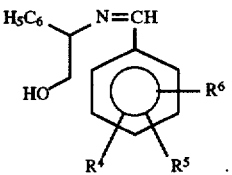

Addition of compounds of formula

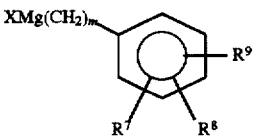

where X is chlorine, bromine, or iodine, after pretreatment with cerous chloride, to the imines produces adducts of formula

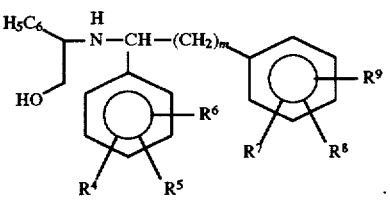

Chiral auxiliary cleavage by treatment with lead tetracetate followed by warm aqueous hydrochloric or sulfuric acid gives the compounds of formula III. To prepare compounds of formula III where m is 0, compounds of formula

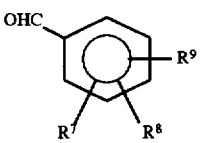

and

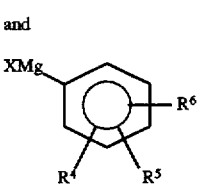

may also be used in place of VII and IX, respectively. These methods are described in M. J. Wu et al., *J. Org. Chem.* 56, 1340 (1991) and M. K. Mokhallalati et al., *Synth. Commun.*, 23, 2055 (1993).

Additional methods for the preparation of compounds of formula III from compounds of formula VII and XI include:

1. Addition of compounds of formula

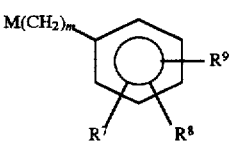

(where M is lithium or sodium or magnesium monochloride, monobromide or monoiodide) to the N-trimethylsilylaldimine of the compounds of formula VII using the method described in D. J. Hart et al., *J. Org. Chem.*, 48, 289 (1983). Likewise, compounds of formula III where m is 0 may also be prepared with the compounds of formula

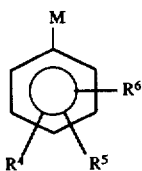

and XI;

2. Formation of the imine of the compounds of formula VII with 4-methoxyaniline, addition of compounds of formula XIII where M is lithium the presence of a chiral ligand, and cleavage of the 4-methoxyphenyl group provides the amines III in optically active form. These methods are described in I. Inoue, *Tet.*, 50, 4429 (1994). Likewise, compounds of formula III where m is 0 may also be prepared with compounds of formula XI and XIV where M in XIV is lithium.

The compounds of formula IV are commercially available or may be prepared by Friedel-Crafts acylation of a compound of formula

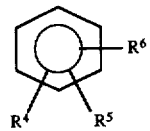   XV with a compound of formula

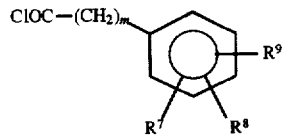   XVI or where m is 0, of a compound of formula

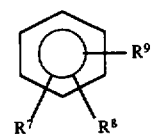   XVII with a compound of formula

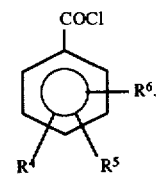   XVIII

Typically, acid chlorides of formula XVI and XVIII may be prepared from the corresponding carboxylic acids by treatment with thionyl chloride or oxalyl chloride in methylene chloride solution, either optionally in the presence of catalytic N,N-dimethyl-formamide.

Compounds of formula IV may also be prepared by oxidation, for example with Jones' reagent, of compounds of formula VI.

Alternatively, compounds of formula IV where m is 1 may be obtained from compounds of formula XVIII and compounds of formula

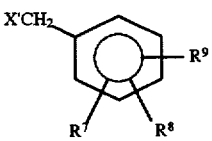   XIX where X' is chlorine or bromine following the procedures described in M. Iyoda et al., *Tet. Lett.*, 26, 4777 (1985).

Compounds of formula VI are obtained by addition of a compound of formula XIII to a compound of formula VII or where m is 0, by addition of a compound of formula XIV, to a compound of formula XI.

Reduction of compounds of formula IV with a reducing agent such as sodium borohydride in a solvent such as ethanol also provides alcohols of formula VI. To prepare the optically active alcohols of formula VI where m is one, the ketone IV where m is one is reduced with a chiral reducing agent as described in D. J. Mathre et al., *J. Org. Chem.*, 58, 2880 (1993).

The aldehydes of formulas VII and XI are commercially available or are prepared from the analogous benzyl alcohols, benzoic acids, aryl halides, benzonitriles, benzyl halides, etc. by methods discussed in the series *Compendium of Organic Synthetic Methods* (John Wiley & Sons).

Certain substituents $R^1$, $R^2$ and $R^3$ may be incompatible with the synthetic route outlined above. To prepare the compounds of formula I containing these substituents the following modifications may be used.

Where $R^1$, $R^2$ or $R^3$ is hydroxyl, the compound of formula II is prepared with the hydroxyl group protected, for example, as a benzyl or trialkylsilyl ether. After coupling of II with III, the protecting group is removed to provide the compound of formula I. The installation and removal of such protecting groups are discussed in *Protective Groups in Organic Synthesis* by T. W. Greene (John Wiley & Sons).

Where $R^1$, $R^2$ or $R^3$ is amino, the compound of formula I where that substituent is nitro is prepared according to the synthetic methodology outlined above. This compound is then reduced to provide the compound of formula I bearing the amino group. Reduction of nitro groups to amino groups may be carried out, for example, by hydrogenation over a catalyst such as Raney Nickel in a solvent such as tetrahydrofuran or by treatment with tin (II) chloride in a solvent such as ethyl acetate.

Where two of the three substituents $R^1$, $R^2$ and $R^3$ together with the benzene ring to which they are attached form a benzimidazole, benzimidazol-2-one, or benzotriazole, the compound of formula I where these two substituents are amino groups is prepared according to the synthetic methodology outlined above. This diamino compound is then carbonylated to provide the compound of formula I that is a benzimidazol-2-one. Such carbonylations may be carried out, for example, with phosgene in aqueous hydrochloric acid solution or with other carbonylating agents such as triphosgene or 1,1'-carbonyldiimidazole.

To provide the compound of formula I that is a benzotriazole, the diamino compound is treated with nitrous acid, for example, by addition of sodium nitrite to a solution of the diamino compound in methanol, acetic acid and aqueous hydrochloric acid.

To provide the compound of formula I that is a benzimidazole the diamino compound is treated with formic acid or triethyl orthoformate or with carbon disulfide and barium hydroxide followed by hydrogenation over Raney Nickel. These and other benzimidazole formation methods are discussed in *Comprehensive Org. Chem.*, Volume IV, editors: chapter-(17.3) M. R. Grimmett; volume-P. G. Sammes; Series-D. Barton and W. D. Ollis.

Certain substituents $R^4$, $R^5$, $R^6$, $R^7$, $R^8$ and $R^9$ may be incompatible with the synthetic route outlined above. To prepare the compounds of formula I containing these substituents the following modifications may be used.

Where one of these substituents is hydroxyl, the compound of formula III is prepared with the hydroxyl group protected, for example, as a benzyl or trialkylsilyl ether. After coupling of II with III, the protecting group is removed to provide the compound of formula I. The installation and removal of such protecting groups are discussed in *Protective Groups in Organic Synthesis* by T. W. Greene (John Wiley & Sons).

Where one of these substituents is an alkoxycarbonyl, carboxy, aminocarbonyl functional group, the compound of formula I where that substituent is either of the other two of these functional groups may be prepared according to the synthetic methodology outlined above. This is then converted to the desired compound of formula I. For example, if the desired compound of formula I is substituted with a carboxy group, then the corresponding compound of formula I containing an alkoxycarbonyl or an aminocarbonyl group may be prepared and converted to the carboxy compound. Likewise, if the desired substituent is an aminocarbonyl group, either a carboxy group or an alkoxycarbonyl group may serve as its precursor. Additionally, the compounds of formula I substituted by alkylaminocarbonyl or dialkylaminocarbonyl groups are available from the compounds of formula I substituted by alkoxycarbonyl or carboxy groups. Analogously, the compounds of formula I substituted by alkoxycarbonylmethyl, carboxymethyl, or aminocarbonylmethyl groups may be prepared from the compounds of formula I substituted by either of the other two of these functional groups, and the compounds of formula I substituted by alkylaminocarbonylmethyl or dialkylaminocarbonylmethyl groups are available from the compounds of formula I substituted by alkoxycarbonylmethyl or carboxymethyl groups. Numerous methods for the interconversion of these functional groups are described in the series *Compendium of Organic Synthetic Methods* (John Wiley & Sons).

Alternatively, where one of the substituents $R^4$, $R^5$, $R^6$, $R^7$, $R^8$ or $R^9$ in the desired compound of formula I contains an amide (amiocarbonyl, alkylaminocarbonyl, dialkylaminocarbonyl, aminocarbonylmethyl, alkylaminocarbonylmethyl, or dialkylaminocarbonylmethyl), the corresponding amine III bearing that amide substituent is employed as described above. The amine III may be prepared from an analogous amine in which that substituent contains an ester (alkoxycarbonyl or alkoxycarbonylmethyl) in place of the amide. The ester-containing amine may be prepared by the routes outlined above; it may be converted to the corresponding amide-containing amine by 1) protection of the basic amino group for example as the t-butoxycarbonyl derivative; 2) conversion of the ester to the amide; and 3) deprotection of the amino group.

In cases where one of the substituents $R^4$, $R^5$, $R^6$, $R^7$, $R^8$ or $R^9$ in amine III is methoxycarbonylmethyl it is possible to prepare the amine III using a cyanomethyl group as a protected fore of the methoxycarbonylmethyl group. For example, to prepare the compound of formula III where m is one, $R^4$ is p-$CH_3OCOCH_2$-, and $R^5$, $R^6$, $R^7$, $R^8$ and $R^9$ are all hydrogen, one may begin with p-bromomethylbenzoic acid. Reaction with potassium cyanide in aqueous ethanol at reflux gives p-cyanomethylbenzoic acid, which is converted to the acid chloride (XVIII) and then, by reaction with benzyl bromide (XIX), to IV as described above. Fusion of IV with ammonium formate followed by heating in methanolic hydrogen chloride, as described above, not only effects reductive amination, but also converts the cyanomethyl group to a methoxycarbonylmethyl group and the required compound III is obtained.

It is recognized that more than one of the synthetic modifications useful for the incorporation of certain substituents may be simultaneously employed.

In any of the above reactions, it may be necessary to protect certain substituents by using protecting groups as known by those skilled in the art.

Compounds of the formula I where the substituents are as defined above are novel compounds provided that: a) when m is zero and $R^4$ to $R^9$ are all hydrogen and two of the three substituents $R^1$, $R^2$ and $R^3$ together with the carbons to which they are attached fore a heterocycle, the heterocycle must be other than a 2-hydroxypyridine or a 3,4-dihydro-2-hydroxy-pyridine; and b) when m is zero and $R^1$ and $R^4$ to $R^9$ are all hydrogen, then $R^2$ and $R^3$ may not be 1) hydrogen and hydroxymethyl, 2) alkyl and alkyl, 3) alkyl and alkoxy, 4) alkoxy and alkoxy, or 5) chloro and chloro.

Preferred novel compounds of formula I are those where the substituents are as defined above provided that: a) where two of the three substituents $R^1$, $R^2$ and $R^3$ together with the carbons to which they are attached form a heterocycle, the heterocycle is other than a 2-hydroxypyridine or a 3,4-dihydro-2-hydroxypyridine; b) when m is zero and $R^1$ and $R^4$ to $R^9$ are all hydrogen, then $R^2$ and $R^3$ may not be 1) hydrogen and hydroxymethyl, 2) hydrogen and aminocarbonyl, 3) alkyl and alkoxy, 4) chloro and alkoxy, 5) chloro and chloro, 6) alkoxy and alkoxy or 7) alkyl and alkyl; c) when $R^4$ to $R^9$ are all hydrogen or halogen and $R^1$ and $R^2$ are hydrogen, then $R^3$ may not be hydrogen, phenyl or alkoxy; and d) when $R^1$ and $R^4$ to $R^9$ are all hydrogen, then $R^2$ and $R^3$ may not both be alkyl.

Preferred compounds of formula I are also those where the hydroxyl stereocenter has the (S) configuration. Additional preferred compounds of formula I are those where $R^1$, $R^4$, $R^7$ and $R^8$ are hydrogen and m is one; and those where $R^1$, $R^4$, $R^7$, $R^8$ and $R^9$ are hydrogen and m is one.

The most preferred compounds of formula I are those where the hydroxyl stereocenter has the (S) configuration, the Amine stereocenter has the (R) configuration and m is one.

The present compounds of formula I have activity at the beta 3 adrenergic receptor and are therefore useful, for example, in the treatment of diabetes, obesity, gastrointestinal diseases (such as inflammatory bowel disease, irritable bowel syndrome, nonspecific diarrhea, and peptic ulcer) and achalasia.

Thus a composition containing one (or a combination) of the compounds of this invention, may be administered to a species of mammal (e.g., humans) suffering from diabetes, obesity, an intestinal hypermotility disorder or achalasia as treatment therefor.

A single dose, or two to four divided daily doses, provided on a basis of about 0.1 to 100 mg per kilogram of body weight per day, preferably about 1 to 15 mg per kilogram of body weight per day is appropriate. The substance is preferably administered orally, but intranasal, transdermal and parenteral routes such as the subcutaneous, intramuscular, intravenous or intraperitoneal routes can also be employed.

The compounds of this invention can also be formulated in combination with $beta_1$/$beta_2$ adrenergic blockers such as propranolol and nadolol or stimulants such as salbutalmol.

The compounds of formula I can be formulated for use in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Based on the literature, it is expected that these compounds may be useful for other indications such as treatment of depression and stress, regulation of intraocular pressure, treatment of conditions associated with increased protein breakdown such as during convalescence afar surgery, treatment of hypertriglyceridemia, hypercholesterolemia, atherosclerotic and cardiovascular diseases, and for increasing high density lipoprotein levels. In addition, it is expected that these compounds may be useful as feed additives for fattening or improving weight gain or increasing lean body mass in animals and may therefore be used to decrease birth mortality and increase post-natal survival rates in animals.

In addition, based on the literature, compounds of formula I are expected to be useful for improving healing and preventing stomach ulcers (K. Kuratani et al., *J. Pharmacol. Exp. Ther.* 270, 559 (1994)). The compounds of formula I are also expected to be useful for regulating core temperature.

The following examples and preparations describe the invention and are illustrative rather than limiting. It should be understood that there may be other embodiments which fall within the spirit and scope of the invention as defined by the claims appended hereto.

EXAMPLE 1

(S)-1-[[Bis(4-methoxyphenyl)methyl]amino]-3-phenoxy-2-propanol

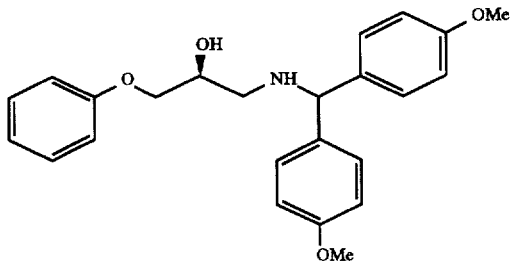

A. (S)-(Phenoxymethyl)oxirane

The title compound was prepared according to the methods described in J. M. Klunder et al., *J. Org. Chem.*, 54, 1295 (1989). The ee of the title compound was shown to be 99.2% by chiral HPLC analysis. Its precursor ((2S)-(+)-glycidyl 3-nitrobenzenesulfonate) was recrystallized four times from ethanol to 99.8% ee.

B. (S)-1-[[Bis(4-methoxyphenyl)methyl]amino]-3-phenoxy-2-propanol 1. 4,4'-Dimethoxydiphenylmethylamine The title compound was prepared according to Y. Ito et al., *Tetrahedron*, 45, 5767 (1989).

2. (S)-1-[[Bis(4-methoxyphenyl)methyl]amino]-3-phenoxy-2-propanol

To the title 1 compound (m.w. 243, 340 mg, 1.4 mmol, 1.6 equiv.) at room temperature under argon was added N-(trimethylsilyl)acetamide (m.w. 131, 197 mg, 1.5 mmol, 1.7 equiv.). The resulting solution was stirred at room temperature for two hours. To the mixture was then added the title A compound (m.w. 150, 135 mg, 0.9 mmol). The resulting solution was heated for two days at 65°–70° C., then for three days at 180° C. The mixture was cooled to room temperature and diluted with ethyl acetate (~20 ml). About 15 g of chipped ice and 4 mL conc. hydrochloric acid were added. This mixture was stirred for four hours, allowing the ice to melt. The mixture was basified to pH 12 by addition of 1M aq. sodium hydroxide. The ethyl acetate layer was removed, and the aqueous layer was then extracted three times with methylene chloride (100 ml). The various organic extracts were combined, dried over sodium sulfate, and then concentrated to a thick oil, which was purified by silica gel chromatography eluting with 2% (10% conc. aq. ammonium hydroxide/methanol)/methylene chloride to produce 232 mg of the title compound as a white powder (66% yield).

TLC: $R_f$=0.35 in 5% (10% conc. aq. ammonium hydroxide/methanol)/methylene chloride, p-anisaldehyde stain, UV.

MS: $(M+H)^+$ at 394.

EXAMPLE 2

(2S)-1-[[1-(3,4-Dimethoxyphenyl)-2-phenylethyl]amino]-3-phenoxy-2-propanol, trifluoroacetate (1:1) salt

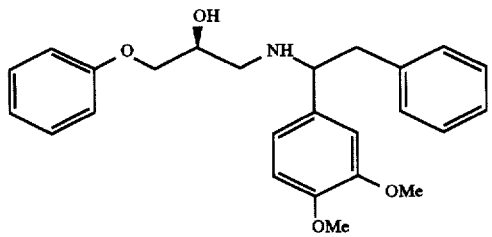

A. 1-(3,4-Dimethoxyphenyl)-2-phenylethylamine

The title compound was prepared according to I. P. G. Nerlekar et al., *J. Karnatak Univ.*, 2, 58 (1957), abstracted by Chemical Abstracts 53:14051.

B (2S)-1-[[1-(3,4-Dimethoxyphenyl)-2-phenylethyl]amino]-3-phenoxy-2-propanol, trifluoroacetate (1:1) salt The title compound was prepared from the title A compound (m.w. 257, 500 mg, 1.9 mmol, 1.9 equiv.), N-(trimethylsilyl)acetamide (m.w. 131, 275 mg, 2.1 mmol, 2.1 equiv.), and the title A compound of Example 1 ((S)-(phenoxymethyl)oxirane: m.w. 150, 150 mg, 1.0 mmol) according to the procedures described for the preparation of the title 2 compound of step B of Example 1 with the following modifications. In this case heating was carried out for three days at 65°–70° C. After silica gel chromatography eluting with 5% (10% conc. aq. ammonium hydroxide/methanol)/methylene chloride, the chromatographed product was dissolved in ether (~30 mL) and then trifluoroacetic acid (m.w. 114, d 1.5, 0.230 mL, 0.34 g, 3.0 mmol, 3.0 equiv.) was added. The solution was then coevaporated several times with toluene, then with methylene chloride, and finally with ether. This produced 340 mg of the title compound as a white powder (64% yield).

TLC: $R_f$=0.3 in 5% (10% conc. aq. ammonium hydroxide/methanol)/methylene chloride, p-anisaldehyde stain, UV.

MS: $(M+H)^+$ at 408.

EXAMPLE 3

(2S)-1-[[1-(3,4-Dimethoxyphenyl)-2-phenylethyl]amino]-3-(4-fluorophenoxy)-2-propanol, trifluoroacetate (1:1) salt

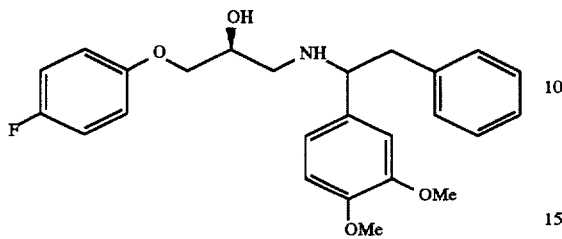

A. (S)-[(4-Fluorophenoxy)methyl]oxirane

The title compound was prepared following the procedures described for the preparation of the title A compound of Example 1 ((S)-(phenoxymethyl)oxirane) except using p-fluorophenol as a starting material. The title compound was derived from chiral precursor of 99.86% ee (chiral HPLC analysis).

TLC: Rf=0.9 in 5% ethyl acetate/hexane, p-anisaldehyde stain, UV.

$^{13}$C NMR (67.8 MHz, CDCl$_3$) δ: 149.0, 141.2, 127.1, 120.2, 107.6, 69.6, 50.0, 44.5.

B. (2S)-1-[[1-(3,4-Dimethoxyphenyl)-2-phenylethyl]amino]-3-(4-fluorophenoxy)-2-propanol trifluoroacetate (1:1) salt To 1-(3,4-dimethoxyphenyl)-2-phenylethylamine (m.w. 257, 500 mg, 1.9 mmol, 1.9 equiv.) at room temperature under argon was added N-(trimethylsilyl)acetamide (m.w. 131, 275 mg, 2.1 mmol, 2.1 equiv.). The mixture was stirred as a melt at 60° C. for two hours. To the mixture was then added the title A compound (m.w. 168, 168 mg, 1.0 mmol). The resulting solution was heated for three days at 100° C. The mixture was cooled to room temperature and diluted with ethyl acetate (~10 mL). About 10 mL of chipped ice and 4 mL conc. hydrochloric acid were added. This mixture was stirred for four hours, allowing the ice to melt. The mixture was basified to pH 12 by addition of 1M aq. sodium hydroxide. The ethyl acetate layer was removed, and the aqueous layer was then extracted four times with methylene chloride (100 mL). The various organic extracts were combined, dried over sodium sulfate, and then concentrated to a thick oil, which was purified by silica gel chromatography eluting with 5% (10% conc. aq. ammonium hydroxide/methanol)/methylene chloride. The chromatographed product was dissolved in ether (~30 mL) and then trifluoroacetic acid (m.w. 114, d 1.5, 0.230 mL, 0.34 g, 3.0 mmol, 3.0 equiv.) was added. The solution was then coevaporated several times with toluene, then with methylene chloride, and finally with ether. This produced 340 mg of the title compound as a white powder (63% yield).

MS: (M+H)$^+$ at 426.

EXAMPLE 4

(2S) -3-([1,1'-Biphenyl]-2-yloxy)-1-[[1-(3,4-dimethoxy-phenyl)-2-phenylethyl]amino]-2-propanol, trifluoroacetate (1:1) salt

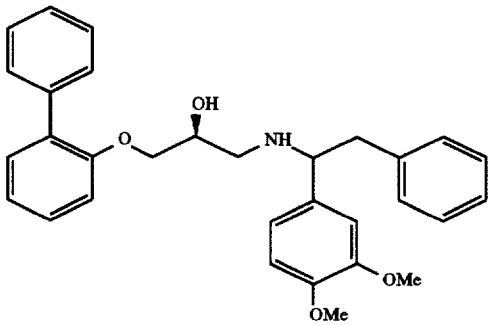

A. (S)-[([1,1'-Biphenyl]-2-yloxy)methyl]oxirane

Prepared from o-phenylphenol in >62% yield using procedures described in J. M. Klunder et al., *J. Org. Chem.*, 54, 1295 (1989). The precursor to the title compound, (2S)-(+)-glycidyl 3-nitrobenzenesulfonate was recrystallized four times from ethanol to 99.8% ee (determined by chiral HPLC analysis). The title compound was shown to be 99.0% ee by chiral HPLC analysis.

TLC: R$_f$=0.5 in 25% ethyl acetate/hexane, p-anisaldehyde stain, UV.

$^{13}$C NMR (CDCl$_3$) δ: 155, 148, 132, 129, 128, 127 126, 121, 113, 69, 50, 44.

B. (2S)-3-([1,1'-Biphenyl]-2-yloxy)-1-[[1-(3,4-dimethoxyphenyl)-2-phenylethyl]amino]-2-propanol, trifluoroacetate (1:1) salt The title compound was prepared according to the procedures described for the preparation of the title B compound of Example 3, but using the title A compound (m.w. 226, 226 mg, 1.0 mmol). In this case the product was purified by silica gel chromatography eluting with 3% methanol/methylene chloride. Some product was left behind in mixed fractions. The purified product was then dissolved in a few milliliters of ether and treated with trifluoroacetic acid (m.w. 114, 125 mg, 1.1 mmol). The resulting solution was coevaporated several times with toluene to remove excess trifluoroacetic acid, then several times with methylene chloride. Trituration with ether produced 210 mg of the title compound as a pale yellow solid (34% yield (corrected for 4% impurity)).

MS: (M+H)$^+$ at 484.

EXAMPLE 5

(2S)-1-[[1-(3,4-Dimethoxyphenyl)-2-phenylethyl]amino]3-(4-hydroxyphenoxy)-2-propanol

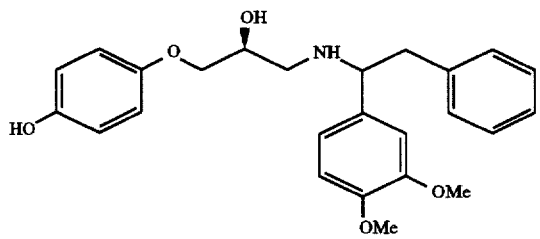

A. (S)-[[4-(Phenylmethoxy)phenoxy]methyl]oxirane

Made following procedures described for the preparation of the title A compound of Example 1 ((S)-(phenoxymethyl)

-oxirane) except using 4-benzyloxyphenol as a starting material. The title compound was derived from chiral precursor of 99.86% ee (chiral HPLC analysis).

TLC: $R_f$=0.7 in 30% ethyl acetate/hexane, p-anisaldehyde stain, UV.

$^{13}$C NMR (67.8 MHz, CDCl$_3$) δ: 153, 154, 137.1, 128.5, 127.8, 127.4, 115.7, 115.6, 70.5, 69.4, 50.2, 44.6.

B. (2S)-1-[[1-(3,4-Dimethoxyphenyl)-2-phenylethyl]amino]-3-[4-(phenylmethoxy)phenoxy]-2- propanol The title compound was prepared according to the procedures described for the preparation of the title B compound of Example 3 but using the title A compound (m.w. 256, 256 mg, 1.0 mmol). In this case the title compound was chromatographed eluting with 3% (10% conc. aq. ammonium hydroxide/methanol)/methylene chloride. The product, a yellow oil, was not salted.

TLC: $R_f$=0.5 in 3% (10% conc. aq. ammonium hydroxide/methanol)/methylene chloride, p-anisaldehyde stain, UV.

$^{13}$C NMR (67.8 MHz, CDCl$_3$) δ: 154, 153, 148, 147, 138.5, 135, 134, 129.2, 128.3, 128.2, 127.7, 127.3, 126.2, 119.2, 115.6, 115.3, 110.8, 109.9, 71, 70.4, 69, 68, 63, 64, 55.6, 49, 50, 45.1.

C. (2S)-1-[[1-(3,4-Dimethoxyphenyl)-2-phenylethyl]amino]-3-(4-hydroxyphenoxy)-2-propanol To a solution of the title B compound (m.w. 513, 100 mg, 0.19 mmol) in methanol (2 mL) at room temperature under argon was added acetic acid (glacial, 17.5M, 0.217 ml, 3.8 mmol, 20 equiv.) and 10% Pd/C (50 mg). The mixture was sparged with hydrogen for 10–15 minutes, then maintained under a hydrogen balloon for one and one half hours. The catalyst was filtered off and the filtrate was concentrated and chromatographed on silica gel eluting with 15% (10% conc. aq. ammonium hydroxide/methanol)/methylene chloride. The title compound was isolated in 95% purity as 60 mg of light brown solid (71% yield (corrected for 5% impurity)) after trituration with ether.

TLC: $R_f$=0.3 in 20% (10% conc. aq. ammonium hydroxide/methanol)/methylene chloride, p-anisaldehyde stain, UV.

MS: (H+H)$^+$ at 424.

EXAMPLE 6

(2S)-1-[[1-(3,4-Dimethoxyphenyl)-2-phenylethyl]amino]-3-(2-hydroxyphenoxy)-2-propanol

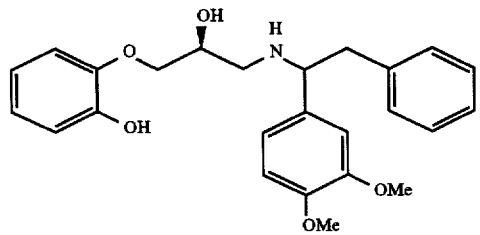

A. (S)-[[2-(Phenylmethoxy)phenoxy]methyl]oxirane

Made in 63% yield by the method described for the title A compound of Example 1 ((S)-(phenoxymethyl)oxirane), except using 2-benzyloxyphenol as the starting material. The title compound was derived from chiral precursor of 99.86% ee (chiral HPLC analysis).

TLC: $R_f$=0.5 in 30% EtOAc/hexane, p-anisaldehyde stain, UV.

B. (2S)-1-[[1-(3,4-Dimethoxyphenyl)-2-phenylethyl]amino]-3-[2-(phenylmethoxy)phenoxy]-2-propanol The title compound was prepared according to the procedures described for the preparation of the title B compound of Example 3 but using the title A compound. In this case the title compound was purified by silica gel chromatography eluting with 2% (10% conc. aq. ammonium hydroxide/methanol)/methylene chloride. The product, an oil, was not salted.

TLC: $R_f$=0.3 in 3% (10% conc. aq. ammonium hydroxide/methanol)/methylene chloride, p-anisaldehyde stain, UV.

C. (2S)-1-[[1-(3,4-Dimethoxyphenyl)-2-phenylethyl]amino]-3-(2-hydroxyphenoxy)-2-propanol To a solution of the title B compound (m.w. 513, 550 mg impure, ~415 mg net, ~0.8 mmol) in methanol (5 mL) at room temperature under argon was added acetic acid (glacial, 17.5M, 0.183 mL, 3.2 mmol, ~4 equiv.) and 10% Pd/C (70 mg). The mixture was sparged with hydrogen for 10–15 minutes, then maintained under a hydrogen balloon for five hours. At this point 20 mg more catalyst was added and the sparging repeated. The mixture was then maintained under 1 atm hydrogen for eight hours, at which point the reaction was nearly complete by TLC. The catalyst was filtered off and the filtrate was concentrated and chromatographed on silica gel eluting with 2% (10% cons. aq. ammonium hydroxide/methanol)/methylene chloride. The title compound was isolated as 50 mg of white powder after trituration with ether (15% isolated yield—a large amount of material was left behind in mixed fractions).

TLC: $R_f$=0.5 in 10% (10% cons. aq. ammonium hydroxide/methanol)/methylene chloride, p-anisaldehyde stain, UV.

MS: (M+H)$^+$ at 424.

EXAMPLE 7

(2S)-1-[[1-(3,4-Dimethoxyphenyl)-2-phenylethyl]amino]-3-(3-hydroxyphenoxy)-2-propanol

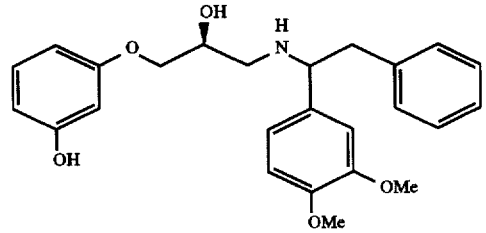

A. (S)-[[3-(Phenylmethoxy)phenoxy]methyl]oxirane

Made in 51% yield by the method described for the title A compound of Example 1 ((S)-(phenoxymethyl)oxirane) except using 3-benzyloxyphenol (made as described in Ponpipom, M. M., et al., *J. Med. Chem.*, 30, 136 (1987)) as the starting material. The title compound was derived from chiral precursor of 99.86% ee (chiral HPLC analysis).

TLC: $R_f$=0.8 in 30% ethyl acetate/hexane, p-anisaldehyde stain, UV.

$^{13}$C NMR (67.8 MHz, CDCl$_3$) δ: 160, 159, 136.8, 129.9, 128.5, 127.9, 127.5, 107.6, 107.4, 102.0, 70.0, 68.7, 50.0, 44.7.

B. (2S)-1-[[1-(3,4-Dimethoxyphenyl)-2-phenylethyl]amino]-3-[3-(phenylmethoxy)phenoxy]-2-propanol The title compound was prepared according to the procedures described for the preparation of the title B compound of Example 3 but using the title A compound. In this case the title compound was purified by silica gel chromatography eluting with 2% (10% conc. aq. ammonium hydroxide/methanol)/methylene chloride. The product, an oil, was not salted.

TLC: $R_f$=0.3 in 5% (10% conc. aq. ammonium hydroxide/methanol)/methylene chloride, p-anisaldehyde stain, UV.

17

C. (2S)-1-[[1-(3,4-Dimethoxyphenyl)-2-phenylethyl]-amino]-3-(3-hydroxyphenoxy)-2-propanol To a solution of the title B compound (m.w. 513, 388 mg, 0.76 mmol) in methanol (5 mL) at room temperature under argon was added acetic acid (glacial, 17.5M, 0.087 ml, 1.5 mmol, ~2 equiv.) and 10% Pd/C (100 mg). The mixture was sparged with hydrogen for 10–15 minutes, then maintained under a hydrogen balloon for four hours. At this point 120 mg more catalyst was added and the sparging was repeated. The mixture was then maintained under 1 atm hydrogen for six hours, at which point the reaction was complete by TLC. The catalyst was filtered off and the filtrate was concentrated and chromatographed on silica gel eluting with a stepwise gradient of 1–5% (10% conc. aq. ammonium hydroxide/methanol)/methylene chloride. The title compound was isolated as 150 mg of white powder after trituration with ether (47% yield).

TLC: $R_f$=0.5 in 10% (10% conc. aq. ammonium hydroxide/methanol)/methylene chloride, p-anisaldehyde strain, UV.

MS: (M+H)$^+$ at 424.

EXAMPLE 8

(2S)-1-(4-Amino-3-nitrophenoxy)-3-[[1-(3,4-dimethoxy-phenyl)-2-phenylethyl]amino]-2-propanol

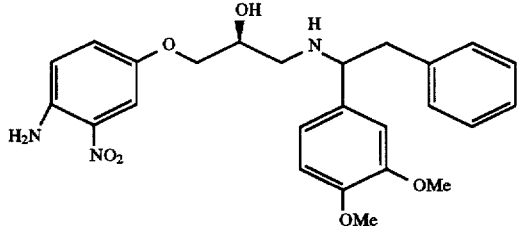

A. (S)-[(4-Amino-3-nitrophenoxy)methyl]oxirane

Made in 45% yield by the method described for the title A compound of Example 1 ((S)-(phenoxymethyl)oxirane) except using 4-amino-3-nitrophenol as a starting material. The title compound was derived from chiral precursor of 99.86% ee (chiral HPLC analysis).

TLC: $R_f$=0.8 in 5% methanol/methylene chloride, p-anisaldehyde stain, UV.

B. (2S)-1-(4-Amino-3-nitrophenoxy)-3-[[1-(3,4-dimethoxyphenyl)-2-phenylethyl]amino]-2-propanol The title compound was prepared according to the procedures described for the preparation of the title B compound of Example 3 but using the title A compound. In this case the title compound was purified by silica gel chromatography eluting with 2% methanol/methylene chloride. The title compound, a dark orange powder, was not salted.

TLC: $R_f$=0.2 in 2% (10% conc. aq. ammonium hydroxide/methanol)/methylene chloride, p-anisaldehyde stain, UV.

MS: (M+H)$^+$ at 468.

18

EXAMPLE 9

(2S)-1-(1H-Benzotriazol-5-yloxy)-3-[[1-(3,4dimethoxyphenyl)-2-phenylethyl]amino]-2-propanol

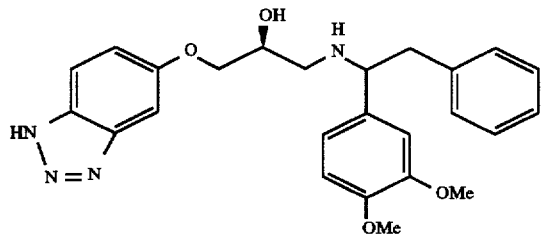

A. (2S)-1-(3,4-Diaminophenoxy)-3-[[1-(3,4-dimethoxyphenyl)-2-phenylethyl]amino]-2-propanol, trihydrochloride A slurry of W-6 Raney Nickel in water (6.6 g) was washed five times with water, five times with isopropanol, and five times with tetrahydrofuran (freshly distilled from potassium benzophenone ketyl), and then placed under argon at room temperature. To this slurry was added the title compound of Example 8 ((2S)-1-(4-Amino-3-nitrophenoxy)-3-[[1-(3,4-dimethoxyphenyl)-2-phenylethyl]amino]-2-propanol: m.w. 467, 770 mg, 1.6 mmol) as a solution in tetrahydrofuran (to total 24 mL of tetrahydrofuran). The mixture was sparged with hydrogen for 10–15 minutes, and then maintained under 1 atm hydrogen for five hours. The supernatant was then pipetted into a flask containing ~1M aq. hydrochloric acid (4.8 mL, ~4.8 mmol). The resulting solution was concentrated to remove tetrahydrofuran and then lyophilized to 410 mg of orange powder, which was shown by NMR to be ~60% pure title compound (28% corrected yield); Note: the title compound is unstable as the free base.

TLC (as free base): $R_f$=0.45 in 10% (10% conc. aq. ammonium hydroxide/methanol)/methylene chloride, p-anisaldehyde stain, UV.

B. (2S)-1-(1H-Benzotriazol-5-yloxy)-3-[[1-(3,4-dimethoxyphenyl)-2-phenylethyl]amino]-2-propanol To a solution of the title A compound (m.w. 547, 200 mg, ~60% pure, ~120 mg net, ~0.22 mmol) in water (1.0 mL) and acetic acid (0.1 mL) at 0° C. under argon was added NaNO$_2$ (1.0M aq., 0.24 mL, 0.24 mmol, 1 equiv.). The mixture was allowed to warm to room temperature. The starting material was consumed after fifteen minutes reaction time as judged by analytical HPLC. The reaction was quenched by addition of sodium hydroxide (1.0M, 0.48 mL, 0.48 mmol, 2.0 equiv.) The reaction solution was coevaporated several times with toluene and then with methylene chloride, combined with material from an earlier run, and then chromatographed on silica gel eluting with 5% (10% conc. aq. ammonium hydroxide/methanol)/methylene chloride. The title compound was isolated as 10 mg of tan powder. The title compound was not stable to the chromatography conditions used.

MS: (M+H)$^+$ at 449.

EXAMPLE 10

(2S)-1-(2-Amino-3-nitrophenoxy)-3-[[1-(3,4-dimethoxyphenyl)-2-phenylethyl]amino]-2-propanol

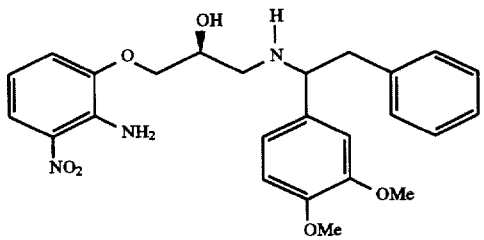

A. (S)-[(2-Amino-3-nitrophenoxy)methyl oxirane

See J. M. Klunder et al., *J. Org. Chem.*, 54, 1295 (1989) for the preparation of chiral aryl glycidyl ethers and F. Aigbirhio et al., *Tet. Asymmetry*, 3, 539 (1992) for a preparation of the title compound.

Under argon at room temperature 2-amino-3-nitrophenol (1.03 g, 6.68 mmol) was dissolved in dry dimethylformamide (20 mL) with stirring. To the resulting red solution was added carefully 60% sodium hydride oil dispersion (0.29 g unwashed, 0.17 g net, 7.25 mmol) which caused gas evolution, a mild exotherm, and a color change to deep purple. After one hour (2S)-(+)-glycidyl 3-nitrobenzenesulfonate (1.60 g, 6.18 mmol, 99.8% ee) was added. After four hours satd. aq. ammonium chloride solution (about 25 mL) was carefully added to quench excess sodium hydride. Water was added to dissolve precipitated solid, and the mixture was extracted four times with diethyl ether. After drying over anhydrous sodium sulfate, the combined organic layers were evaporated and then coevaporated with toluene to remove residual dimethylformamide. Flash chromatography (silica gel, 0.5% to 1.0% methanol in methylene chloride stepwise gradient) was performed to isolate pure title compound (0.54 g, 42% yield) as an orange solid. The optical purity of the title compound was 99.1% ee as determined by chiral HPLC (Chiracel OD collators, hexane/2-propanol/diethylamine 85:15:0.1 eluant).

TLC (50% ethyl acetate in hexane—anisaldehyde, UV) $R_f$

| | |
|---|---|
| 2-amino-3-nitrophenol | 0.50 |
| (2S)-(+)-glycidyl 3-nitrobenzenesulfonate | 0.35 |
| the title compound | 0.43 |

$^{13}$C NMR (67.8 MHz in CDCl$_3$) δ: 146.9, 137.2, 131.8, 118.2, 115.3, 114.4, 70.4, 49.8, 44.5.

B. (2S)-1-(2-Amino-3-nitrophenoxy)-3-[[1-(3,4-dimethoxyphenyl)-2-phenylethyl]amino]-2-propanol In an oven-dried flask under argon a mixture of racemic 1-(3,4-dimethoxyphenyl)-2-phenylethylamine (0.37 g, 1.44 mmol) and N-(trimethylsilyl)acetamide (0.23 g, 1.76 mmol) was melted and stirred at 90° C. for two hours. To this was added the title A epoxide (0.16 g, 0.76 mmol) and the homogeneous mixture was heated at 103°–118° C. for 20 hours. After cooling to room temperature, about 20 mL each of ethyl acetate and 6M aq. hydrochloric acid were added, and after stirring for about ten minutes, a homogeneous mixture had formed. After two to four hours addition of several volumes of ethyl acetate produced a mixture of two layers. Aq. sodium hydroxide (1.0M) was added until the mixture was basic. Ice was added to cool the mixture and the organic layer was separated. Four further extractions with methylene chloride were performed, and the organic layers were combined, dried over anhydrous sodium sulfate, and evaporated. Flash chromatography (silica gel, 2% methanol in methylene chloride), provided the title compound (0.30 g, 84% yield) as an orange solid foam.

TLC (5% [10% conc. aq. NH$_3$ in methanol] in methylene chloride-anisaldehyde, UV) $R_f$.

| | |
|---|---|
| 1-(3,4-dimethoxyphenyl)-2-phenylethylamine | 0.30 |
| the title A compound | 0.89 |
| silylated title B compound intermediate | 0.80 |
| the title B compound | 0.36 |

MS by chemical ionization: (M+H)$^+$@468 and M.$^-$@467.

EXAMPLE 11

(2S)-1-(2,3-Diaminophenoxy)-3-[[1-(3,4-dimethoxyphenyl)-2-phenylethyl]amino]-2-propanol

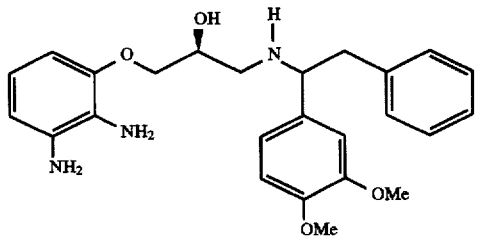

At room temperature 50% Raney Nickel/water slurry (0.6 g) was dried by twice adding 2-propanol, stirring, and removing the supernatant after the Raney Nickel was allowed to settle. The 2-propanol was then exchanged out for freshly distilled tetrahydrofuran by the same method using tetrahydrofuran fife times. About one fish of the resulting Raney Nickel/tetrahydrofuran slurry was then added to a stirring solution of the title compound of Example 10 ((2S)-1-(2-Amino-3-nitrophenoxy)-3-[[1-(3,4-dimethoxyphenyl)-2-phenylethyl]amino]-2-propanol: 101 mg, 0.22 mmol) in dry tetrahydrofuran (4 mL) at room temperature. The mixture was sparged with hydrogen for five minutes before placing under a hydrogen balloon for three hours. Disappearance of the original yellow color coincided with complete consumption of starting material by TLC. The mixture was filtered through a short plug of silica gel eluting with tetrahydrofuran. The eluant was evaporated to a gum, which upon coevaporation with diethyl ether became a white solid, the title compound (0.09 g, 94% yield).

TLC (10% [10% conc. aq. NH$_3$ in methanol] in methylene chloride-anisaldehyde, UV) $R_f$:

| | |
|---|---|
| the title compound of Example 10 | 0.51 |
| the title compound of Example 11 | 0.32 |

MS by chemical ionization: (M+H)$^+$@438.

EXAMPLE 12

(2S)-1-Dihydro-4-[3-[[1-(3,4-dimethoxyphenyl)-2-phenylethyl]-amino]-2-hydroxypropoxy]-2H-benzimidazol-2-one

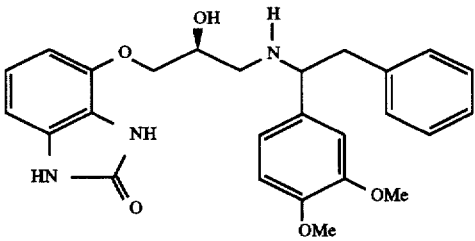

See U.S. Pat. No. 4,346,093 for the synthesis of a related benzimidazolone by this method.

At room temperature phosgene gas was passed over a stirring solution of the title compound of Example 11 ((2S)-1-(2,3-Diaminophenoxy)-3-[[1-(3,4-dimethoxyphenyl)-2-phenylethyl]amino]-2-propanol: 0.05 g, 0.11 mmol) in approximately 0.2M aq. hydrochloric acid solution (approximately 5 mL) for one hour. A white precipitate formed. The mixture was then allowed to stand open overnight. The mixture was made basic by addition of 1.0M aq. sodium bicarbonate solution. After brine was added, the mixture was extracted four times with methylene chloride/ethyl acetate (3:1). The combined organic extracts were dried over anhydrous sodium sulfate and evaporated to a gum, which upon coevaporation with diethyl ether became an off-white solid, nearly pure desired product (59 mg, about 80% yield). To remove trace impurities, this material was flash chromatographed (silica gel, 0% to 15% [10% conc. aq. NH$_3$ in methanol] in methylene chloride, stepwise gradient) and, by coevaporation with diethyl ether, made into a white solid, the title compound.

TLC (10% [10% conc. aq. NH$_3$ in methanol] in methylene chloride-anisaldehyde, UV) R$_f$:

| the title compound of Example 11 | 0.28 |
| the title compound of Example 12 | 0.25 |

MS by chemical ionization: (M+H)$^+$@464 and (M+H)$^-$@462.

EXAMPLE 13

(2S)-1-(1H-Benzotriazol-4-yloxy)-3-[[1-(3,4-dimethoxyphenyl)-2-phenylethyl]amino]-2-propanol

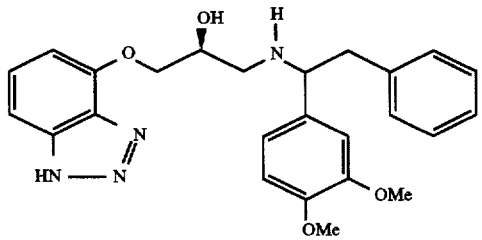

See U.S. Pat. No. 4,346,093 for the synthesis of a related benzotriazole by this method.

Impure, air-stable trihydrochloride salt of the title compound of Example 11 ((2S)-1-(2,3-Diaminophenoxy)-3-[[1-(3,4-dimethoxyphenyl)-2-phenylethyl]amino]-2-propanol) was prepared by dissolving impure title compound of Example 11 in methanol at room temperature, adding 1.00M aq. hydrochloric acid solution (3.3 equiv.), rotoevaporating, and then lyophilizing to obtain a solid. A solution of this material (0.06 g gross, 0.11 mmol net) in water (0.2 mL) and acetic acid (0.05 mL) was cooled to 0° C. Upon addition of 1.0M aq. sodium nitrite solution (0.12 ml, 0.12 mmol), a precipitate formed. Additional water (0.2 mL) and methanol (0.5 ml,) were added, and the mixture was warmed to room temperature to dissolve all solids. TLC indicated complete reaction. After addition of 1.0M aq. sodium hydroxide solution (0.24 mL), the mixture was coevaporated with methanol and toluene to remove acetic acid and water. The residue was flash chromatographed (silica gel, 5% [10% conc. aq. NH$_3$ in methanol] in methylene chloride) and coevaporation with diethyl ether gave, as an off-white solid, the title compound (29 mg, 59% yield).

TLC (10% [10% conc. aq. NH$_3$ in methanol] in methylene chloride-anisaldehyde, UV) R$_f$:

| the title compound of Example 11 | 0.27 |
| the title compound of Example 13 | 0.25 |

MS by chemical ionization: (M+H)$^+$@449.

EXAMPLE 14

(2S)-1-[(1,2-Diphenylethyl)amino]-3-phenoxy-2-propanol, monohydrochloride

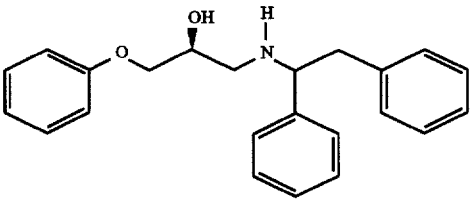

Under argon a mixture of the title A compound of Example 1 ((S)-(phenoxymethyl)oxirane; optical purity of 99.2% ee; 0.20 g, 1.3 mmol) and 1,2-diphenylethylamine (0.43 g, 2.2 mmol) was heated to 135° C. and stirred for 2.5 hours. After cooling to room temperature the mixture was flash chromatographed (silica gel, 0.5% to 0.75% [10% conc. aq. NH$_3$/MeOH]/CH$_2$Cl$_2$ stepwise gradient) to provide the free base of the title compound as an oil. A solution of the free base in diethyl ether was prepared, and HCl gas was passed over the solution until insoluble oil stopped forming at the surface. The oil soon solidified. The solid was broken up and filtered, washing with ether. After drying under vacuum, the title compound was obtained as a white solid (0.39 g, 78% yield).

TLC (2.5% [10% conc. aq. NH$_3$ in MeOH] in CH$_2$Cl$_2$-anisaldehyde, UV) R$_f$:

| (S)-(phenoxymethyl)oxirane | 0.86 |
| 1,2-diphenylethylamine | 0.17 |
| the title compound | 0.35 |

MS by electrospray ionization: (M+H)$^+$@348.

EXAMPLE 15

(2S)-1-[[1-[4-(Difluoromethoxy)phenyl]-2-(4-fluorophenyl)ethyl]-amino]-3-phenoxy-2-propanol, monohydrochloride

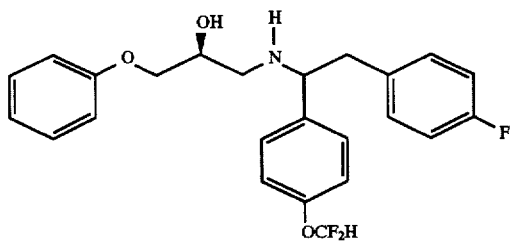

A. 4-(Difluoromethoxy)benzoic add

Difluorochloromethane was bubbled through a 75° C. i-PrOH (100 mL) solution containing commercially available methyl 4-hydroxybenzoate (7.5 g, 5.0 mmol) and t-BuOK (5.6 g, 5 mmol). After two hours, 4 additional g of t-BuOK was added and the reaction continued two hours. The reaction was diluted with $H_2O$ and extracted with EtOAc (3×). The organic phases were washed with $H_2O$ (3×), brine, dried over $Na_2SO_4$ and concentrated to yield 12 g of methyl 4-difluoromethoxy-benzoate as an oil. The crude methyl 4-difluoromethoxy-benzoate was refluxed two hours in 2:1 MeOH/$H_2O$ containing KOH (3.4 g, 61 mmol) followed by dilution with $H_2O$. After washing the aqueous phase 2× with 1:1 $Et_2O$/hexane and then acidification to pH 1 with 2.5N $H_2SO_4$, the title compound was collected by filtration as a white solid (8.6 g).

B. α-((4-Difluoromethoxy)phenyl)-4-fluorobenzene ethanamine

To a stirred suspension of Zn powder (3.3 g, 50 mmol) and Pd(PPh$_3$)$_4$ (1.45 g, 1.25 mmol) in DME (20 mL) under $N_2$, was added 10 mL of DME containing 4-fluorobenzyl bromide (4.9 g, 26 mmol) and 4-difluoromethoxybenzoyl chloride (4.7 g, 25 mmol) (prepared by refluxing 4-difluoromethoxybenzoic acid in $SOCl_2$). After stirring 40 hours at 20° C., the reaction was diluted with EtOAc and $H_2O$, filtered through Celite, and then concentrated. The crude product was dissolved in EtOAc, washed with brine, dried over $Na_2SO_4$, and then concentrated to 10 g of crude product. Chromatography on silica gel using 1:2 $CH_2Cl_2$/hexane eluted 4 g of 1-((4-difluoromethoxy)phenyl)-2-(4-fluorophenyl)ethanone. This was heated with about 10 equivalents of ammonium formate at about 170° C. for about one day before cooling, dilution with water, and extraction with EtOAc several times. The combined extracts were dried over sodium sulfate and evaporated to provide the N-formylated title compound. This was heated at 90° C. in a sealed tube with about a 1:1 mixture of methanol and conc. aq. HCl for several hours. After cooling to room temperature, the mixture was diluted with water and washed twice with $Et_2O$ before basification with aq. NaOH solution. This was extracted several times with EtOAc, and the combined extracts were dried over sodium sulfate and evaporated. After pretreatment with excess TFA, the title amine was purified from α-(4-hydroxyphenyl)-4-fluorobenzeneethanamine by preparative HPLC chromatography using a $C_{18}$ HPLC column eluting with 50% solvent B (solvent A=10% MeOH, 90% $H_2O$, 0.1% TFA; solvent B=90% MeOH, 10% $H_2O$, 0.1% TFA), followed by liberation from the TFA salt by standard procedures.

C. (2S)-1-[[1-[4-(Difluoromethoxy)phenyl]-2-(4-fluorophenyl)ethyl]amino]-3-phenoxy-2-propanol, monohydrochloride Under argon a mixture of the title A compound of Example 1 ((S)-(phenoxymethyl)oxirane; optical purity of 99.2% ee; 0.08 g, 0.53 mmol) and impure title B compound (about 85% pure, 0.17 g net, 0.61 mmol) was heated to 135° C. and stirred for 2.5 hours. After cooling to room temperature the mixture was flash chromatographed (silica gel, 0.5% to 0.8% [10% conc. aq. $NH_3$/MeOH]/$CH_2Cl_2$ stepwise gradient) to provide the free base of the title compound as an oil. A solution of the free base in diethyl ether was prepared, and HCl gas was passed over the solution, but the mixture remained homogeneous. Addition of hexane caused an oil to form. The supernatant was removed, and the oil was dissolved in methanol. This solution was diluted with water, and partially evaporated to remove most of the methanol. Lyophilization gave the title compound (0.07 g, 30% yield) as a fluffy material that later collapsed into a gum.

TLC (2.5% [10% conc. aq. $NH_3$ in MeOH] in $CH_2Cl_2$-anisaldehyde, UV) $R_f$:

| | |
|---|---|
| (S)-(phenoxymethyl)oxirane | 0.86 |
| the title B compound | 0.16 |
| the title compound | 0.27 |

MS by chemical ionization: $(M+H)^+$@432.

EXAMPLE 16

(2S)-1-[[1-[4-(Methylsulfonyl)phenyl]-2-phenylethyl]amino]-3-phenoxy-2-propanol, monohydrochloride

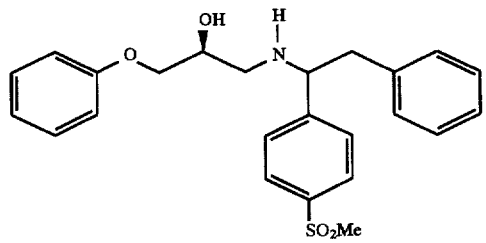

A. α-[4-(Methylthio)phenyl]benzeneethanol

To 50 mL of 2.0M benzylmagnesium chloride in THF solution (100 mmol) stirring under argon at 48° C. was added over 10 minutes a solution of 13.9 g of 4-methylthiobenz-aldehyde (91 mmol) in 15 ml of freshly distilled THF. Exotherm caused the mixture to reflux. For 25 minutes after the addition was complete reflux was maintained with further heating. The homogeneous mixture was cooled to room temperature, and while stirring, 30 mL of sat. aq. ammonium chloride solution (about 2 equiv.) was added. This addition was also exothermic and resulted in the formation of a paste plus supernatant. The supernatant was decanted, and several times the paste was stirred with additional THF and the supernatant removed. The combined supernatants were diluted with toluene, dried over sodium sulfate, and evaporated. This provided 22.7 g of 90% pure title compound as a yellow solid (20.4 g net, 92% yield).

TLC (25% EtOAc in hexane—anisaldehyde, UV) $R_f$:

| | |
|---|---|
| 4-methylthiobenzaldehyde | 0.50 |
| the title compound | 0.38 |

$^{13}C$ NMR (68 MHz, CDCl$_3$) δ: 140.7, 137.8, 137.5, 129.4, 128.5, 126.6, 126.4, 74.8, 45.9, 15.9.

B. α-[4-(Methylsulfonyl)phenyl]benzeneethanol

A solution of the title A compound (15.8 g, 90% pure, 14.2 g net, 58 mmol) in 300 mL methylene chloride was stirred at 0° C. with a pH 8 solution of K$_2$HPO$_4$ (42 g, 240 mmol) and KH$_2$PO$_4$ (5.0 g, 37 mmol) in 500 ml of water. To this mixture was added 15 g of 75% mCPBA (11 g net, 65 mmol). TLC at five minutes indicated that much of the starting material had been converted to a very low R$_f$ material (putative sulfoxide). Addition of 27 g more oxidant (20 g net, 117 mmol) caused the formation of white precipitate, and TLC after 15 minutes indicated complete consumption of starting material and disappearance of putative sulfoxide with the formation of the title compound. The aqueous layer was separated, and the organic layer was filtered. The filtrate was washed sequentially with 200 mL of 1.0M aq. Na$_2$S$_2$O$_3$, 200 mL of 1.0M aq. sodium bicarbonate, and 200 mL of 1.0M aq. NaOH. After drying over sodium sulfate and solvent evaporation, 17.4 g of 90% pure title compound (15.7 g net, 98% yield) was obtained as an off-white solid.

TLC (50% EtOAc in hexane—anisaldehyde, UV) R$_f$:

| | |
|---|---|
| the title A compound | 0.80 |
| putative sulfoxide | 0.05 |
| the title B compound | 0.36 |

MS by chemical ionization: (M+NH$_4$)$^+$@294.

$^{13}$C NMR (68 MHz, CDCl$_3$) δ: 150.2, 139.1, 137.0, 129.4, 128.5, 127.2, 126.8, 74.2, 45.8, 44.3.

C. 1-[4-(Methylsulfonyl)phenyl]-2-phenyl-1-ethanone

A solution of the title B compound (10.5 g, 90% pure, 9.5 g net, 34 mmol) in 100 mL, acetone was stirred at 0° C. under argon as Jones' reagent was slowly added until a red-orange color persisted (12 mL). Blue-green precipitate formed. Excess oxidant was quenched with 2-propanol after 15 minutes. Ethyl acetate and 3M aq. sodium bisulfite were added, and the mixture was stirred at room temperature until all solids had dissolved. This was extracted with ethyl acetate four times, and the combined extracts, diluted with methylene chloride, were dried over sodium sulfate and evaporated. This provided 10.0 g of 85% pure title compound (8.5 g net, 91% yield) as a wet white solid.

TLC (50% EtOAc in hexane—anisaldehyde, UV) R$_f$:

| | |
|---|---|
| the title B compound | 0.33 |
| the title C compound | 0.48 |

$^{13}$C NMR (68 MHz, CD$_3$SOCD$_3$) δ: 197.2, 144.3, 140.1, 134.5, 129.8, 129.2, 128.4, 127.4, 126.6, 45.1, 43.2.

D. N-[1-[4-(Methylsulfonyl)phenyl]-2-phenylethyl]-formamide

A mixture of the title C compound (5.5 g, 85% pure, 4.6 g net, 17 mmol) and ammonium formate (12.6 g, 200 mmol) was heated to 180° C. with stirring for four hours. The mixture, which eventually became homogeneous, was cooled before addition of water and ethyl acetate. A white precipitate was produced. The mixture was extracted four times with ethyl acetate and four times with methylene chloride. The mixture still contained precipitate, which was filtered, water washed, and air-dried to provide 0.48 g of pure title compound (9% yield) as a white solid. The combined extracts were dried over sodium sulfate and evaporated to provide 6.72 g of impure title compound (66% pure, 4.43 g net, 86% yield) for a total yield of 95%.

TLC (50% EtOAc in hexane—anisaldehyde, UV) R$_f$:

| | |
|---|---|
| the title C compound | 0.57 |
| the title D compound | 0.06 |

MS by chemical ionization: (M+NH$_4$)$^+$@321 and (M+H)$^+$@304.

E. α-[4-(Methylsulfonyl)phenyl]benzeneethanamine

A sealed tube containing a mixture of 25 mL each of methanol and conc. aq. HCl and 2.05 g of impure title D compound (1.61 g net, 5.3 mmol) was one third immersed in a 60° C. oil bath for four hours. Solid title D compound dissolved with stirring. The mixture was cooled to 0° C., and was poured into 450 mL of 1.0M aq. NaOH stirring at 0° C. An oil formed and was extracted with methylene chloride (three times). The combined extracts were dried over sodium sulfate and evaporated. This provided 1.38 g of pure title compound (95% yield) as a pale yellow solid.

TLC (100% EtOAc—anisaldehyde, UV) R$_f$:

| | |
|---|---|
| the title D compound | 0.47 |
| the title E compound | 0.11 |

$^1$NMR (270 MHz, CDCl$_3$): δ 8 1.51 (bs, 2H), 2.81 (dd, J=8, 13 Hz, 1H), 2.98 (dd, J=5, 13 Hz, 1H), 3.04 (s, 3H), 4.30 (dd, J=5, 8 Hz, 1H), 7.10–7.35 (m, 5H), 7.55 (d, J=8 Hz, 2H), 7.87 (d, J=8 Hz, 2H). $^{13}$C NMR (68 1 MHz, CDCl$_3$) δ: 151.9, 138.9, 137.9, 129.1, 128.4, 127.4, 127.3, 126.6, 57.0, 46.2, 44.4.

F. (2S)-1-[[1-[4-(Methylsulfonyl)phenyl]-2-phenylethyl]-amino]-3-phenoxy-2-propanol, monohydrochloride Under argon a mixture of the title A compound of Example 1 ((S)-(phenoxymethyl)oxirane; optical purity of 99.2% ee; 0.07 g, 0.47 mmol) and the title E compound (0.16 g, 0.58 mmol) was heated to 135° C. and stirred for 2.5 hours. After cooling to room temperature the mixture was flash chromatographed (silica gel, 1.0% to 1.5% [10% conc. aq. NH$_3$/MeOH]/CH$_2$Cl$_2$ stepwise gradient) to provide the free base of the title compound as an oil. A solution of the free base in diethyl ether was prepared, and HCl gas was passed over the solution until solid precipitate stopped forming at the surface. The solid was filtered, washing with ether. After drying under vacuum, the title compound was obtained as an off-white solid (95% pure, containing 3% diethyl ether, 0.17 g, 0.16 g net, 74% yield).

TLC (2.5% [10% conc. aq. NH$_3$ in MeOH] in CH$_2$Cl$_2$-anisaldehyde, UV) R$_f$:

| | |
|---|---|
| (S)-(phenoxymethyl)oxirane | 0.88 |
| the title E compound | 0.10 |
| the title compound | 0.19 |

MS by electrospray ionization: (M+H)$^+$@426.

EXAMPLE 17

[S-(R*,S*)]-1-[[1-(1,3-Benzodioxol-5-yl)-2-phenylethyl]amino]-3-phenoxy-2-propanol

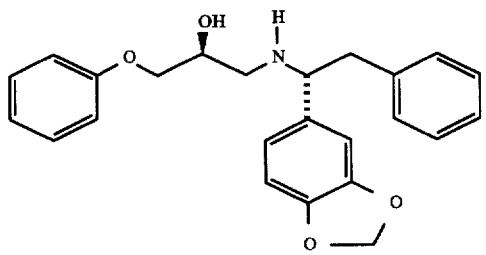

A. (R,E)-β-[[(1,3-Benzodioxol-5-yl)methylene]amino]-benzeneethanol

To piperonal (m.w. 150, 12.0 g, 80.0 mmol) in CDCl$_3$ (40 ml) was added (R)-phenylglycinol (Aldrich, m.w. 137, 11.0 g, 80.0 mmol, 1.0 equiv.). The ee of the phenylglycinol was shown to be 98.7% by chiral HPLC analysis. The solution was stirred at room temperature overnight, then with a few grams of sodium sulfate. The mixture was filtered and coevaporated several times with toluene and then several times with methylene chloride to provide the title compound as a yellow oil (21.41 g, 99% yield).

B. [R-(R*,R*)]-β-[[1-(1,3-Benzodioxol-5-yl)-2-phenylethyl]-amino]benzeneethanol, monohydrochloride To THF (freshly distilled from potassium benzophenone ketyl, 300 ml) at room temperature in an oven dried flask was added CeCl$_3$ (m.w. 246.5, 60.0 g, 243 mmol, 3.1 equiv., freshly opened). The mixture was stirred overnight at room temperature under argon. The mixture was chilled to –45° C. and then benzylmagnesium chloride (2.0M in THF, 120 240 mmol, 3.0 equiv.) was added by cannula. This mixture was stirred at –45° C. for 1.5 hours. Then a solution of the title A compound (m.w. 269, 21.2 g, 78.8 mmol) in THF (~50 mL) was added over about 40 minutes. The mixture was allowed to warm to room temperature after 10 minutes more and was then cautiously quenched by addition of 800 ml, of water. This was extracted three times with ~600 mL of methylene chloride, and the extracts were dried (Na$_2$SO$_4$) and concentrated to an oil which was shown by analytical HPLC to contain an 11:1 mixture of the title compound and its diastereomer. The oil was dissolved in 500 mL of ether. To the ether solution was added a solution of methanolic HCl made by cautious addition of AcCl (m.w. 78, 12.5 g, 160 mmol, ~2 equiv.) to ~40 mL of methanol at 0° C. White precipitate formed immediately. The mixture was chilled at 0° C. and the precipitate was filtered and then recrystallized from ~400 mL of MeOH and 1.5 L of ether. After chilling overnight at 0° C. the precipitate (pure title compound, 23.3 g, 74% yield) was collected by filtration, rinsed with ether, and dried under vacuum.

TLC (5% (10% conc. aq. NH$_4$OH/MeOH)/CH$_2$Cl$_2$): Rf:0.65, UV, p-anisaldehyde stain.

$^{13}$C NMR (67.8 MHz, CD$_3$OD) δ: 150.2, 150.0, 136.9, 135.1, 130.9, 130.5, 130.4, 129.6, 129.5, 128.8, 128.1, 124.4, 109.6, 109.2, 103.1, 64.9, 63.5, 63.3, 40.1.

HPLC: YMC ODS S3 6.0×150 mm column, gradient elution with 0–100% B (A=90% H$_2$O, 10% MeOH, 0.2% H$_3$PO$_4$, B=90% MeOH, 10% H$_2$O, 0.2% H$_3$PO$_4$) over 25 minutes, at a flow rate of 1.5 mL/minute with detection at 217 nm, major diastereomer title compound elutes at 19.1 minutes, minor diastereomer elutes at 19.9 minutes.

C. (R)-α-(1,3-Benzodioxol-5-yl)benzeneethanamine

The title B compound (m.w. 398, 21.1 g, 53.1 mmol) was partitioned between ~150 mL of methylene chloride and ~150 ml, of 1M aq. NaHCO$_3$. The organic layer was removed and the aqueous layer was extracted twice more with ~150 mL of methylene chloride. The organic layers were combined, dried over sodium sulfate, and concentrated to a thick oil.

To 800 mL of MeOH at 0° C. under argon was added Pb(OAc)$_4$ (m.w. 443, 30.6 g, 69.1 mmol, 1.3 equiv.). The free-based title B compound was added as a solution in 400 mL methylene chloride over a period of 30–40 minutes. Soon afterward the yellow reaction solution was diluted with 200 ml, of methylene chloride and 10% aq. Na$_2$CO$_3$ (600 ml) was added. The organic layer was removed and the aqueous layer extracted three times with 200 mL of CH$_2$Cl$_2$. The various organic layers were combined, dried over Na$_2$SO$_4$, and concentrated to a brown oil.

The oil was dissolved in a solution of 150 mL of water, 50 mL of MeOH, and 12 mL of conc. aq. HCl. After stirring at 60° C. for six hours, the reaction solution was cooled to room temperature and then basified to pH 12 by addition of 1M aq. NaOH. The organic layer was removed and the aqueous layer was extracted 3 times with ~200 mL of methylene chloride. The organic extracts were combined and dried over sodium sulfate and then concentrated to a thick oil. The oil was dissolved in 500 mL of ether. To the ether solution was added a solution of methanolic HCl made by cautious addition of AcCl (m.w. 78, 12.5 g, 160 mmol, ~3 equiv.) to ~40 mL of methanol at 0° C. White precipitate formed immediately. The mixture was chilled at 0° C. and the precipitate was filtered. After drying under vacuum the precipitate, pure HCl salt of the title compound (9.3 g, 63% yield), was partitioned between ~150 mL, of methylene chloride and ~50 ml, of 1M aq. NaHCO$_3$. The organic layer was removed and the aqueous layer was extracted twice more with ~150 mL of methylene chloride. The organic layers were combined, dried over sodium sulfate, and concentrated to afford as a brown solid (9.1 g) incompletely free-based amine. This material was Kugelrohr distilled at 0.06–0.08 torr at 175°–190° C. to provide 5.6 g of clear, colorless oil. Chiral HPLC (GITC derivative, PGC column, MeCN/H$_2$O 85:15 eluant) indicated the optical purity of the title compound to be 95.1% ee.

TLC (10% (10% conc aq NH$_4$OH/MeOH)/CH$_2$Cl$_2$): R$_f$=0.8, UV, p-anisaldehyde stain.

$^{13}$C NMR (67.8 MHz, CDCl$_3$) δ: 46.5, 57.2, 100.8, 106.7, 107.9, 119.4, 126.2, 128.3, 129.2, 138.9, 139.7, 146.3, 147.5.

Elemental Analysis:

|   | Calculated | Found |
|---|---|---|
| C | 74.67 | 74.81 |
| H | 6.27 | 6.53 |
| N | 5.80 | 5.87 |

D. [S-(R*,S*)]-1-[[1-(1,3-Benzodioxol-5-yl)-2-phenylethyl]-amino]-3-phenoxy-2-propanol In an oven-dried flask under argon a mixture of the title C compound (95.1% ee, 1.02 g, 4.23 mmol) and N-(trimethylsilyl)acetamide (0.63 g, 4.81 mmol) was melted and stirred at 90° C. for one hour. To this was added the title A compound of Example 1 ((S)-(phenoxymethyl)oxirane; optical purity of 99.2% ee; 0.42 g, 2.80 mmol) and the homogeneous mixture was heated at 120° C. for 20 hours. After cooling to room temperature, about 40 mL each of EtOAc and 6M aq. HCl were added, and after stirring for about 10 minutes, a homogeneous mixture had formed. After two to four hours addition of several volumes of EtOAc produced a mixture of two layers. Aq. NaOH (1.0M) was added until the mixture was basic. Ice was added to cool the mixture and the organic layer was separated. Another extraction with EtOAc was performed, and the combined organic layers diluted with methylene chloride were dried over anhydrous sodium sulfate and evaporated. Flash chromatography (silica gel, 25% to 40% EtOAc in hexane) provided pure title compound (0.99 g, 90% yield) as a white solid.

TLC (5% [10% conc. aq. $NH_3$ in MeOH] in $CH_2Cl_2$-anisaldehyde, UV) $R_f$:

| the title C compound | 0.28 |
| (S)-(phenoxymethyl)oxirane | 0.93 |
| silylated title compound intermediate | 0.93 |
| the title compound | 0.39 |

MS by electrospray ionization: $(M+H)^+$@392.

$^1$H NMR (270 MHz, $CDCl_3$) δ: 2.5–2.7 (m, 2H), 2.8–3.0 (m, 2H), 3.7–3.9 (m, 4H), 5.91 (bs, 2H), 6.6–7.0 (m, 6H), 7.1–7.3 (m, 7H).

$^{13}$C NMR (67.8 1 MHz, $CDCl_3$) δ: 158.5, 147.8, 146.6, 138.5, 137.5, 129.4, 129.2, 128.4, 126.4, 120.9, 120.5, 114.4, 107.9, 107.1, 100.8, 70.4, 68.8, 64.9, 49.7, 45.2.

EXAMPLE 18

[S-R*,R*)]-1-[[1-(1,3-Benzodioxol-5-yl)-2-phenylethyl]amino]-3-phenoxy-2-propanol, trifluoroacetate (1:1)

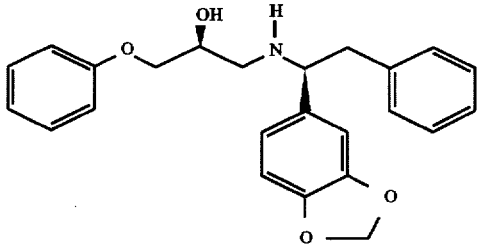

A. [R-(R*,S*)]-B-[[1-(1-Benzodioxol-5-yl)-2-phenylethyl]-amino]benzeneethanol]trifluoroacetate The HCl salt of the title compound was contained within the mother liquors from the preparation of the title B compound of Example 17 as the minor diastereomer. This material was purified (and changed to the TFA salt) by preparative HPLC (YMC SC-15 ODS S3 50×500 mm column, elution with 62% B (A=90% $H_2O$, 10% MeOH, 0.8% TFA, B=90% MeOH, 10% $H_2O$, 0.8% TFA), at a flow rate of 60 mL/minute).

$^{13}$C NMR (67.8 MHz, $CD_3OD$) δ: 150, 136.6, 133.5, 131.0, 130.5, 130.2, 129.5, 128.1, 128.0, 124.4, 109.4, 108.8, 103.1, 64.1, 40.9.

B. (S)-α-(1,3-Benzodioxol-5-yl)benzeneethanamine

This procedure is essentially the same as that used for the preparation of the title C compound or Example 17 with the following modifications: In the various extractions, $Et_2O$ was sometimes substituted for methylene chloride and aq. NaOH was sometimes substituted for aq. $Na_{HCO3}$. Also, the title compound was not distilled. Chiral HPLC (GITC derivative, PGC column, $MeCN/H_2O$ 85:15 eluant) indicated the optical purity of the title compound was 99.4% ee.

C. [S-R*,R*)]-1-[[1-(1,2-Benzodioxol-5-yl)-2-phenylethyl]-amino]-3-phenoxy-2-propanol, trifluoroacetate (1:1)

This step was carried out as in step D of Example 17 except that the reaction was worked up prior to completion, the yield was 70%, and the product free base was an oil. The oil was dissolved in $CH_2Cl_2$. Excess TFA was added, and the solution was evaporated. Coevaporation with toluene, then $CH_2Cl_2$, then $Et_2O$ gave the title compound as a solid foam.

TLC (5% [10% conc. aq. $NH_3$ in MeOH] in $CH_2Cl_2$-anisaldehyde, UV) $R_f$:

| the title B compound | 0.22 |
| (S)-(phenoxymethyl)oxirane | 0.94 |
| silylated title compound intermediate | 0.94 |
| the title compound | 0.33 |

MS by electrospray ionization: $(M+H)^+$@392.

$^1$H NMR (270 1 MHz, $CD_3OD$) δ: 2.87 (dd, J=10, 12 Hz, 1H), 3.15–3.25 (m, 2H), 3.46 (dd, J=4, 13 Hz, 1H), 3.80–4.0 (m, 2H), 4.27 (m, 1H), 4.46 (dd, J=4.7, 11.1 Hz, 1H), 5.95 (m, 2H), 6.7–7.3 (m, 13H).

$^{13}$C NMR (68 MHz, $CD_3OD$) δ: 159.7, 150.1, 150.0, 136.7, 130.5, 130.4, 129.6, 128.2, 128.1, 124.3, 122.3, 115.6, 109.5, 108.9, 103.0, 70.7, 66.5, 65.4, 49, 40.6.

EXAMPLE 19

S-(R*,S*)]-4-[3-[[1-(1,3-Benzodioxol-5-yl)-2-phenylethyl]amino]-2-hydroxypropoxy]-1H-benzimidazol-2(3H)-one

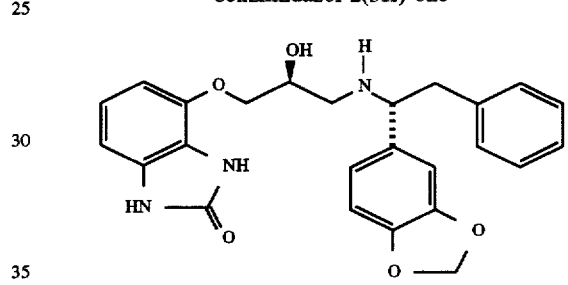

A. [S-(R*,S*)]-1-(2-Amino-3-nitrophenoxy)-3-[[1-(1,3-benzodioxol-5-yl)-2-phenylethyl]amino]-2-propanol This step was performed as described for the analogous step in Example 10, starting with the title C compound of Example 17 and the title A compound of Example 10 (the Example 10A compound used here was prepared by the Aigbirhio method (2-amino-3-nitrophenol, (2S)-(+)-glycidyl 3-nitrobenzenesulfonate (99.8% ee), potassium carbonate, 2-butanone, reflux) which gave the title compound in 44% yield at 90.4% ee), except that during acidic hydrolysis of the silylated intermediate the mixture never became homogeneous even when heated. Flash chromatography (silica gel, 25% to 100% EtOAc in hexane stepwise gradient) provided the title compound in 92% yield as an orange form.

TLC (5% [10% conc. aq. $NH_3$ in MeOH] in $CH_2Cl_2$-anisaldehyde, UV) $R_f$:

| the title C compound of Example 17 | 0.22 |
| the title A compound of Example 10 | 0.82 |
| silylated title compound intermediate | 0.90 |
| the title compound | 0.31 |

$^1$H NMR (270 MHz, $CDCl_3$) δ: 2.5–2.7 (m, 2H), 2.8–3.0 (m, 2H), 3.76 (m, 1H), 3.8–4.0 (m, 3H), 5.92 (s, 2H), 6.42 (bs, 2H), 6.51 (m, 1H), 6.6–6.9 (m, 4H), 7.1–7.3 (m, 5H), 7.69 (dd, J=1.2, 8.8 Hz, 1H).

$^{13}$C NMR (68 MHz, $CDCl_3$) δ: 147.8, 147.1, 146.7, 138.4, 137.3, 137.2, 131.5, 129.1, 128.3, 126.4, 120.4, 117.8, 115.4, 114.4, 108.0, 106.9, 100.9, 71.7, 68.7, 65.0, 49.6, 44.9.

B. [S-(R*.S*)]-4-3-[[1-(1.3-Benzodioxol-5-yl)-2-phenylethyl]-amino]-2-hydroxypropoxy]-1H-benzimidazol-2(3H)-one The title compound was prepared from the title A compound following the procedures described in Examples 11 and 12 with the following modifications: The catalytic hydrogenation step was run for a longer time (16 hours) and using more 50% Raney Nickel/water slurry (3 g per gram of title A compound). The free base of the diaminobenzene intermediate was not isolated. Rather, after filtration through silica gel in THF, the eluant was acidified by addition of 1.0M aq. HCl. This solution was concentrated to a small volume, diluted with water, and again concentrated to a small volume. The resulting brown solution was filtered through Celite to remove a small amount of brown precipitate. The filtrate was then treated with phosgene as described in Example 12. However, during the work-up, basification was performed with aq. NaOH (to pH 11) and extractions were with methylene chloride alone. Flash chromatography (silica gel, 2% to 4% [10% conc. aq. $NH_3$ in MeOH] in $CH_2Cl_2$, stepwise gradient), followed by trituration with diethyl ether and evaporation, provided the title compound as a tan solid in 84% yield.

TLC (10% [10% conc. aq. $NH_3$ in MeOH] in $CH_2Cl_2$-anisaldehyde, UV) $R_f$:

| | |
|---|---|
| the title A compound | 0.54 |
| diaminobenzene intermediate | 0.34 |
| the title compound | 0.29 |

MS by chemical ionization: $(M+H)^+$@448 and $(M-H)^-$@446.

$^1$H NMR (270 MHz, $CD_3OD$) δ: 2.45–2.65 (m, 2H), 2.8–3.0 (m, 2H), 3.79 (t, J=7.0 Hz, 1H), 3.85–4.05 (m, 3H), 5.88 (m, 2H), 6.55–6.7 (m, 4H), 6.84 (s, 1H), 6.93 (t, J=8.2 Hz, 1H), 7.05–7.25 (m, 5H).

$^{13}$C NMR (68 MHz, $CD_3OD$) δ: 157.7, 149.3, 148.1, 144.7, 139.9, 38.0, 131.8, 130.3, 129.3, 127.4, 123.0, 122.2, 120.0, 108.8, 108.4, 106.3, 104.1, 102.2, 72.0, 70.2, 66.5, 50.9, 45.6.

Using the procedures described herein or by modification of the procedures described herein as known by the skilled artisan, the following additional compounds may be prepared. For all divalent substituents listed below, the two points of attachment on the divalent substituent are shown in the same order as the positions to which they are attached. For example, in Example 23, the carbon atom is attached to the ortho position and the nitrogen atom is attached to the meta position.

| Example # | $R_1$ | $R_2$ | $R_3$ | $R_4$ | $R_5$ | $R_6$ | $R_7$ | $R_8$ | $R_9$ | m |
|---|---|---|---|---|---|---|---|---|---|---|
| 20 | m-$CH_2OH$ | H | H | p-MeO | m-MeO | H | H | H | H | 1 |
| 21 | m-$CH_3SO_2NH$ | H | H | p-MeO | m-MeO | H | H | H | H | 1 |
| 22 | m-$CH_3SO_2NH$ | p-OH | H | p-MeO | m-MeO | H | H | H | H | 1 |
| 23 | o,m-C(CH)=CHNH | | H | p-MeO | m-MeO | H | H | H | H | 1 |
| 24 | o,m-OCONH | | H | p-MeO | m-MeO | H | H | H | H | 1 |
| 25 | o,m-NHCONH | | p-OH | p-MeO | m-MeO | H | H | H | H | 1 |
| 26 | o,m-CH=CHCONH | | H | p-MeO | m-MeO | H | H | H | H | 1 |
| 27 | o,m-CH=CHCONH | | p-OH | p-MeO | m-MeO | H | H | H | H | 1 |
| 28 | o,m-N=NNH | | p-OH | p-MeO | m-MeO | H | H | H | H | 1 |
| 29 | p-OH | m-OH | H | p-MeO | m-MeO | H | H | H | H | 1 |
| 30 | m-$CH_3SO_2NH$ | H | H | m,p-$OCH_2O$ | | H | H | H | H | 1 |
| 31 | m-$CH_3SO_2NH$ | p-OH | H | m,p-$OCH_2O$ | | H | H | H | H | 1 |
| 32 | o,m-C(CN)=CHNH | | H | m,p-$OCH_2O$ | | H | H | H | H | 1 |
| 33 | o,m-OCONH | | H | m,p-$OCH_2O$ | | H | H | H | H | 1 |
| 34 | o,m-NHCONH | | p-OH | m,p-$OCH_2O$ | | H | H | H | H | 1 |
| 35 | o,m-CH=CHCONH | | H | m,p-$OCH_2O$ | | H | H | H | H | 1 |
| 36 | o,m-CH=CHCONH | | p-OH | m,p-$OCH_2O$ | | H | H | H | H | 1 |
| 37 | o,m-N=NNH | | H | m,p-$OCH_2O$ | | H | H | H | H | 1 |
| 38 | o,m-N=NNH | | p-OH | m,p-$OCH_2O$ | | H | H | H | H | 1 |
| 39 | m-OH | H | H | m,p-$OCH_2O$ | | H | H | H | H | 1 |
| 40 | p-OH | H | H | m,p-$OCH_2O$ | | H | H | H | H | 1 |
| 41 | p-OH | m-OH | H | m,p-$OCH_2O$ | | H | H | H | H | 1 |
| 42 | m-$CH_2OH$ | H | H | m,p-$OCH_2O$ | | H | H | H | H | 1 |
| 43 | m-$CH_3SO_2NH$ | H | H | p-MeOH | H | H | H | H | H | 1 |
| 44 | m-$CH_3SO_2NH$ | p-OH | H | p-MeOH | H | H | H | H | H | 1 |
| 45 | o,m-C(CN)=CHNH | | H | p-MeOH | H | H | H | H | H | 1 |
| 46 | o,m-OCONH | | H | p-MeOH | H | H | H | H | H | 1 |
| 47 | o,m-NHCONH | | H | p-MeOH | H | H | H | H | H | 1 |
| 48 | o,m-NHCONH | | p-OH | p-MeOH | H | H | H | H | H | 1 |
| 49 | o,m-CH=CHCONH | | H | p-MeOH | H | H | H | H | H | 1 |
| 50 | o,m-CH=CHCONH | | p-OH | p-MeOH | H | H | H | H | H | 1 |
| 51 | o,m-N=NNH | | H | p-MeOH | H | H | H | H | H | 1 |
| 52 | o,m-N=NNH | | p-OH | p-MeOH | H | H | H | H | H | 1 |
| 53 | m-OH | H | H | p-MeOH | H | H | H | H | H | 1 |
| 54 | p-OH | H | H | p-MeOH | H | H | H | H | H | 1 |
| 55 | p-OH | m-OH | H | p-MeOH | H | H | H | H | H | 1 |
| 56 | m-$CH_2OH$ | H | H | p-MeOH | H | H | H | H | H | 1 |
| 57 | H | H | H | p-MeOH | H | H | H | H | H | 1 |
| 58 | m-$CH_3SO_2NH$ | H | H | m-MeOH | H | H | H | H | H | 1 |
| 59 | m-$CH_3SO_2NH$ | p-OH | H | m-MeOH | H | H | H | H | H | 1 |
| 60 | o,m-C(CN)=CHNH | | H | m-MeOH | H | H | H | H | H | 1 |
| 61 | o,m-OCONH | | H | m-MeOH | H | H | H | H | H | 1 |
| 62 | o,m-NHCONH | | H | m-MeOH | H | H | H | H | H | 1 |
| 63 | o,m-NHCONH | | p-OH | m-MeOH | H | H | H | H | H | 1 |
| 64 | o,m-CH=CHCONH | | H | m-MeOH | H | H | H | H | H | 1 |
| 65 | o,m-CH=CHCONH | | p-OH | m-MeOH | H | H | H | H | H | 1 |

-continued

| Example # | R₁ | R₂ | R₃ | R₄ | R₅ | R₆ | R₇ | R₈ | R₉ | m |
|---|---|---|---|---|---|---|---|---|---|---|
| 66 | o,m-N=NNH | | H | m-MeOH | H | H | H | H | H | 1 |
| 67 | o,m-N=NNH | | p-OH | m-MeOH | H | H | H | H | H | 1 |
| 68 | m-OH | H | H | m-MeOH | H | H | H | H | H | 1 |
| 69 | p-OH | H | H | m-MeOH | H | H | H | H | H | 1 |
| 70 | p-OH | m-OH | H | m-MeOH | H | H | H | H | H | 1 |
| 71 | m-CH₂OH | H | H | m-MeOH | H | H | H | H | H | 1 |
| 72 | H | H | H | m-MeOH | H | H | H | H | H | 1 |
| 73 | m-CH₃SO₂NH | H | H | p-CF₂OH | H | H | H | H | H | 1 |
| 74 | m-CH₃SO₂NH | p-OH | H | p-CF₂OH | H | H | H | H | H | 1 |
| 75 | o,m-C(CN)=CHNH | | H | p-CF₂OH | H | H | H | H | H | 1 |
| 76 | o,m-OCONH | | H | p-CF₂OH | H | H | H | H | H | 1 |
| 77 | o,m-NHCONH | | H | p-CF₂OH | H | H | H | H | H | 1 |
| 78 | o,m-NHCONH | | p-OH | p-CF₂OH | H | H | H | H | H | 1 |
| 79 | o,m-CH=CHCONH | | H | p-CF₂OH | H | H | H | H | H | 1 |
| 80 | o,m-CH=CHCONH | | p-OH | p-CF₂OH | H | H | H | H | H | 1 |
| 81 | o,m-N=NNH | | H | p-CF₂OH | H | H | H | H | H | 1 |
| 82 | o,m-N=NNH | | p-OH | p-CF₂OH | H | H | H | H | H | 1 |
| 83 | m-OH | H | H | p-CF₂OH | H | H | H | H | H | 1 |
| 84 | p-OH | H | H | p-CF₂OH | H | H | H | H | H | 1 |
| 85 | p-OH | m-OH | H | p-CF₂OH | H | H | H | H | H | 1 |
| 86 | m-CH₂OH | H | H | p-CF₂OH | H | H | H | H | H | 1 |
| 87 | H | H | H | p-CF₂OH | H | H | H | H | H | 1 |
| 88 | m-CH₃SO₂NH | H | H | p-CONH₂ | H | H | H | H | H | 1 |
| 89 | m-CH₃SO₂NH | p-OH | H | p-CONH₂ | H | H | H | H | H | 1 |
| 90 | o,m-C(CN)=CHNH | | H | p-CONH₂ | H | H | H | H | H | 1 |
| 91 | o,m-OCONH | | H | p-CONH₂ | H | H | H | H | H | 1 |
| 92 | o,m-NHCONH | | H | p-CONH₂ | H | H | H | H | H | 1 |
| 93 | o,m-NHCONH | | p-OH | p-CONH₂ | H | H | H | H | H | 1 |
| 94 | o,m-CH=CHCONH | | H | p-CONH₂ | H | H | H | H | H | 1 |
| 95 | o,m-CH=CHCONH | | p-OH | p-CONH₂ | H | H | H | H | H | 1 |
| 96 | o,m-N=NNH | | H | p-CONH₂ | H | H | H | H | H | 1 |
| 97 | o,m-N=NNH | | p-OH | p-CONH₂ | H | H | H | H | H | 1 |
| 98 | m-OH | H | H | p-CONH₂ | H | H | H | H | H | 1 |
| 99 | p-OH | H | H | p-CONH₂ | H | H | H | H | H | 1 |
| 100 | p-OH | m-OH | H | p-CONH₂ | H | H | H | H | H | 1 |
| 101 | m-CH₂OH | H | H | p-CONH₂ | H | H | H | H | H | 1 |
| 102 | H | H | H | p-CONH₂ | H | H | H | H | H | 1 |
| 103 | m-CH₃SO₂NH | H | H | p-MeO | o,m-CH=CHCH=CH | | H | H | H | 1 |
| 104 | m-CH₃SO₂NH | p-OH | H | p-MeO | o,m-CH=CHCH=CH | | H | H | H | 1 |
| 105 | o,m-C(CN)=CHNH | | H | p-MeO | o,m-CH=CHCH=CH | | H | H | H | 1 |
| 106 | o,m-OCONH | | H | p-MeO | o,m-CH=CHCH=CH | | H | H | H | 1 |
| 107 | o,m-NHCONH | | H | p-MeO | o,m-CH=CHCH=CH | | H | H | H | 1 |
| 108 | o,m-NHCONH | | p-OH | p-MeO | o,m-CH=CHCH=CH | | H | H | H | 1 |
| 109 | o,m-CH=CHCONH | | H | p-MeO | o,m-CH=CHCH=CH | | H | H | H | 1 |
| 110 | o,m-CH=CHCONH | | p-OH | p-MeO | o,m-CH=CHCH=CH | | H | H | H | 1 |
| 111 | o,m-N=NNH | | H | p-MeO | o,m-CH=CHCH=CH | | H | H | H | 1 |
| 112 | o,m-N=NNH | | p-OH | p-MeO | o,m-CH=CHCH=CH | | H | H | H | 1 |
| 113 | m-OH | H | H | p-MeO | o,m-CH=CHCH=CH | | H | H | H | 1 |
| 114 | p-OH | H | H | p-MeO | o,m-CH=CHCH=CH | | H | H | H | 1 |
| 115 | p-OH | m-OH | H | p-MeO | o,m-CH=CHCH=CH | | H | H | H | 1 |
| 116 | m-CH₂OH | H | H | p-MeO | o,m-CH=CHCH=CH | | H | H | H | 1 |
| 117 | H | H | H | p-MeO | o,m-CH=CHCH=CH | | H | H | H | 1 |

What is claimed is:

1. A compound of the formula

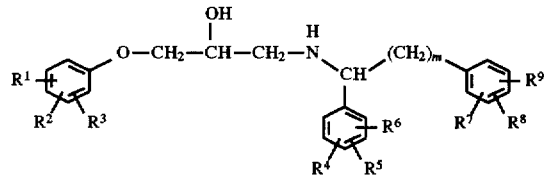

or pharmaceutically acceptable salts thereof where $R^1$, $R^2$ and $R^3$ are independently hydrogen, hydroxy, alkoxy, nitro, amino, alkylsulfonylamino, acylamino, alkylsulfonyl, alkyl, cycloalkyl, phenyl, hydroxymethyl, cyano, aminocarbonyl, halogen or trifluoromethyl;

$R^4$, $R^5$ and $R^6$ are independently hydrogen, alkoxycarbonyl, carboxy, aminocarbonyl, alkylaminocarbonyl, dialkylaminocarbonyl, alkoxycarbonylmethyl, carboxymethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl; or two of the three substituents ($R^4$, $R^5$ and $R^6$) may together be methylenedioxy or benzo such that they together with the benzene ring to which they are attached form naphthyl;

$R^7$, $R^8$ and $R^9$ are independently hydrogen, alkoxycarbonyl, carboxy, aminocarbonyl, alkylaminocarbonyl, dialkylaminocarbonyl, alkoxycarbonylmethyl, carboxymethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl; or two of the three substituents ($R^7$, $R^8$ and $R^9$) may together be methylenedioxy or benzo such that they together with the benzene ring to which they are attached form naphthyl; and m is the integer 0 or 1; provided that a) when $R^1$ is hydrogen, then $R^2$ and $R^3$ may not be halogen and alkyl, chloro and hydrogen, acylamino and hydrogen, acylamino and alkyl, acylamino and halogen, acylamino and aryl, acylamino and hydroxymethyl, acylamino and cycloalkyl, and acylamino and cyano; and when $R^1$ is alkyl, then $R^2$ and $R^3$ may not be acylamino and alkyl; b) when m is 0, and $R^1$ is hydrogen and $R^2$ is alkyl, alkoxy or halogen, and $R^4$ to $R^9$ are hydrogen, then $R^3$ may not be alkyl, alkoxy or halogen; c) when $R^1$ is hydroxymethyl and $R^4$ to $R^9$ are hydrogen, then $R^2$ and $R^3$ may not be hydrogen, alkyl, halogen, hydroxy, alkoxy, or hydroxymethyl; and when $R^1$ and $R^2$ are each hydroxymethyl and $R^4$ to $R^9$ are hydrogen, then $R^3$ may not be hydrogen, alkyl, halogen, hydroxy, or alkoxy; and when $R^1$ and $R^2$ are hydrogen, halogen, hydroxy, alkyl, nitro and alkoxy, $R^3$ may not be hydroxymethyl; d) when $R^1$ is hydrogen, alkyl, halogen or nitro, then at least one of $R^2$ and $R^3$ may not be hydrogen; and e) when m is zero and $R^7$ and $R^8$ are halogen and $R^9$ is hydroxy, at least one of $R^1$ to $R^6$ may not be hydrogen.

2. The compounds as recited in claim 1 wherein the hydroxyl stereocenter has the (S) configuration.

3. The compounds as recited in claim 1 wherein the hydroxyl stereocenter has the (S) configuration, the amine stereocenter has the (R) configuration and m is one.

4. The compounds of claim 2 where $R^1$, $R^4$, $R^7$ and $R^8$ are hydrogen and m is one.

5. The compounds of claim 2 where $R^1$, $R^4$, $R^7$, $R^8$ and $R^9$ are hydrogen and m is one.

6. The compounds as recited in claim 1, which are:

(S)-1-[[bis(4-methoxyphenyl)methyl]amino]-3-phenoxy-2-propanol;

(2S)-1-[[1-(3,4-dimethoxyphenyl)-2-phenylethyl]amino]-3-phenoxy-2-propanol;

(2S)-1-[[1-(3,4-dimethoxyphenyl)-2-phenylethyl]amino]-3-(4-fluorophenoxy)-2-propanol;

(2S)-3-([1,1'-biphenyl]-2-yloxy)-1-[[1-(3,4-dimethoxyphenyl)-2-phenylethyl]amino]-2-propanol;

(2S)-1-[[1-(3,4-dimethoxyphenyl)-2-phenylethyl]amino]-3-(4-hydroxyphenoxy)-2-propanol;

(2S)-1-[[1-(3,4-dimethoxyphenyl)-2-phenylethyl]amino]-3-(2-hydroxyphenoxy)-2-propanol;

(2S)-1-[[1-(3,4-dimethoxyphenyl)-2-phenylethyl]amino]-3-(3-hydroxyphenoxy)-2-propanol;

(2S)-1-(4-amino-3-nitrophenoxy)-3-[[1-(3,4-dimethoxyphenyl)-2-phenylethyl]amino]-2-propanol;

(2S)-1-(2-amino-3-nitrophenoxy)-3-[[1-(3,4-dimethoxyphenyl)-2-phenylethyl]amino]-2-propanol;

(2S)-1-(2,3-diaminophenoxy)-3-[[1-(3,4-dimethoxyphenyl)-2-phenylethyl]-amino]-2-propanol;

(2S)-1-[(1,2-diphenylethyl)amino]-3-phenoxy-2-propanol;

(2S)-1-[[1-[4-(difluoromethoxy)phenyl]-2-(4-fluorophenyl)ethyl]amino]-3-phenoxy-2-propanol;

(2S)-1-[[1-[4-(methylsulfonyl)phenyl]-2-phenylethyl]-amino]-3-phenoxy-2-propanol;

[S-(R*,S*)]-1-[[1-(1,3-benzodioxol-5-yl)-2-phenylethyl]-amino]-3-phenoxy-2-propanol;

[S-R*,R*)]-1-[[1-(1,3-benzodioxol-5-yl)-2-phenylethyl]-amino]-3-phenoxy-2-propanol; or a pharmaceutically acceptable salt thereof.

7. A pharmaceutical composition comprising a pharmaceutically acceptable carrier and a compound of the formula

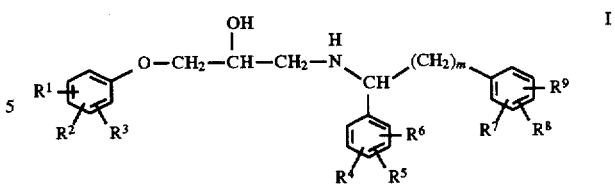

or pharmaceutically acceptable salts thereof where $R^1$, $R^2$ and $R^3$ are independently hydrogen, hydroxy, alkoxy, nitro, amino, alkylsulfonylamino, acylamino, alkylsulfonyl, alkyl, cycloalkyl, phenyl, hydroxymethyl, cyclo, aminocarbonyl, halogen or trifluoromethyl;

$R^4$, $R^5$ and $R^6$ are independently hydrogen, alkoxycarbonyl, carboxy, aminocarbonyl, alkylaminocarbonyl, dialkylaminocarbonyl, alkoxycarbonylmethyl, carboxymethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl; or two of the three substituents ($R^4$, $R^5$ and $R^6$) may together be methylenedioxy or benzo such that they together with the benzene ring to which they are attached form naphthyl;

$R^7$, $R^8$ and $R^9$ are independently hydrogen, alkoxycarbonyl, carbon, aminocarbonyl, alkylaminocarbonyl, dialkylaminocarbonyl, alkoxycarbonylmethyl, carboxymethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl; or two of the three substituents ($R^7$, $R^8$ and $R^9$) may together be methylenedioxy or benzo such that they together with the benzene ring to which they are attached form naphthyl; and m is the integer 0 or 1; provided that a) when $R^1$ is hydrogen, then $R^2$ and $R^3$ may not be halogen and alkyl, chloro and hydrogen, acylamino and hydrogen, acylamino and alkyl, acylamino and halogen, acylamino and aryl, acylamino and hydroxymethyl, acylamino and cycloalkyl, and acylamino and cyano; and when $R^1$ is alkyl, then $R^2$ and $R^3$ may not be acylamino and alkyl; b) when m is 0, and $R^1$ is hydrogen and $R^2$ is alkyl, alkoxy, or halogen, and $R^4$ to $R^9$ are hydrogen, then $R^3$ may not be alkyl, alkoxy or halogen; c) when $R^1$ is hydroxymethyl and $R^4$ to $R^9$ are hydrogen, then $R^2$ and $R^3$ may not be hydrogen, alkyl, halogen, hydroxy, alkoxy, or hydroxymethyl; and when $R^1$ and $R^2$ are each hydroxymethyl and $R^4$ to $R^9$ are hydrogen, then $R^3$ may not be hydrogen, alkyl, halogen, hydroxy, or alkoxy; and when $R^1$ and $R^2$ are hydrogen, halogen, hydroxy, alkyl, nitro and alkoxy, $R^3$ may not be hydroxymethyl; d) when $R^1$ is hydrogen, alkyl, halogen or nitro, then at least one of $R^2$ and $R^3$ may not be hydrogen; and e) when m is zero and $R^7$ and $R^8$ are halogen and $R^9$ is hydroxy, at least one of $R^1$ to $R^6$ may not be hydrogen.

8. A pharmaceutical composition comprising a beta$_1$ or beta$_2$ adrenergic blocker or stimulant, a pharmaceutically acceptable carrier and a compound of formula

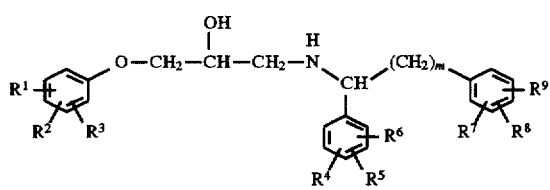

or pharmaceutically acceptable salts thereof where $R^1$, $R^2$ and $R^3$ are independently hydrogen, hydroxy, alkoxy, nitro, amino, alkylsulfonylamino, acylamino, alkylsulfonyl, alkyl, cycloalkyl, phenyl, hydroxymethyl, cyano, aminocarbonyl, halogen, or trifluoromethyl;

$R^4$, $R^5$ and $R^6$ are independently hydrogen, alkoxycarbonyl, carboxy, aminocarbonyl, alkylaminocarbonyl, dialkylaminocarbonyl, alkoxycarbonylmethyl, carboxymethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl; or two of the three substituents ($R^4$, $R^5$ and $R^6$) may together be methylenedioxy or benzo such that they together with the benzene ring to which they are attached from naphthyl;

$R^7$, $R^8$ and $R^9$ are independently hydrogen, alkoxycarbonyl, carboxy, aminocarbonyl, alkylaminocarbonyl, dialkylaminocarbonyl, alkoxycarbonylmethyl, carboxyethyl, aminocarbonylmethyl, alkylaminocarbonylmethyl, dialkylaminocarbonylmethyl, hydroxy, alkoxy, di- or trifluoromethoxy, halogen, trifluoromethyl, cycloalkyl or alkyl; or two of the three substituents ($R^7$, $R^8$ and $R^9$) may together be methylenedioxy or benzo such that they together with the benzene ring to which they are attached form naphthyl; and m is the integer 0 or 1; provided that a) when $R^1$ is hydrogen, then $R^2$ aria $R^3$ may not be halogen aria alkyl, chloro and hydrogen, acylamino and hydrogen, acylamino and alkyl, acylamino and halogen, acylamino and aryl, acylamino and hydroxymethyl, acylamino and cycloalkyl, and acylamino and cyano; and when $R^1$ is alkyl, then $R^2$ and $R^3$ may not be acylamino and alkyl; b) when m is 0, and $R^1$ is hydrogen and $R^2$ is alkyl, alkoxy or halogen, and $R^4$ to $R^9$ are hydrogen, then $R^3$ may not be alkyl, alkoxy or halogen; c) when $R^1$ is hydroxymethyl and $R^4$ to $R^9$ are hydrogen, then $R^2$ and $R^3$ may not be hydrogen, alkyl, halogen, hydroxy, alkoxy, or hydroxymethyl; and when $R^1$ and $R^2$ are each hydroxymethyl and $R^4$ to $R^9$ are hydrogen, then $R^3$ may not be hydrogen, alkyl, halogen, hydroxy, or alkoxy; and when $R^1$ and $R^2$ are hydrogen, halogen, hydroxy, alkyl, nitro and alkoxy, $R^3$ may not be hydroxymethyl; d) when $R^1$ is hydrogen, alkyl, halogen or nitro, then at least one of $R^2$ and $R^3$ may not be hydrogen; and e) when m is zero and $R^7$ and $R^8$ are halogen and $R^9$ is hydroxy, at least one of $R^1$ to $R^6$ may not be hydrogen.

9. A method for treating diabetes comprising administering to a mammalian specie in need thereof a therapeutically effective amount of a composition of claim 7.

10. A method for treating obesity comprising administering to a mammalian specie in need thereof a therapeutically effective amount of a composition of claim 7.

11. A method for treating intestinal hypermotility comprising administering to a mammalian specie in need thereof a therapeutically effective amount of a composition of claim 7.

12. A method for treating achalasia comprising administering to a mammalian specie in need thereof a therapeutically effective amount of a composition of claim 7.

13. A method for treating diabetes comprising administering to a mammalian specie in need thereof a therapeutically effective amount of a composition of claim 8.

14. A method for treating obesity comprising administering to a mammalian specie in need thereof a therapeutically effective amount of a composition of claim 8.

15. A method for treating intestinal hypermotility comprising administering to a mammalian specie in need thereof a therapeutically effective amount of a composition of claim 8.

16. A method for treating achalasia comprising administering to a mammalian specie in need thereof a therapeutically effective amount of a composition of claim 8.

* * * * *

UNITED STATES PATENT AND TRADEMARK OFFICE
CERTIFICATE OF CORRECTION

PATENT NO.    : 5,723,489
DATED         : March 3, 1998
INVENTOR(S)   : Philip M. Sher et al It is certified that error appears in the above-identified patent and that said Letters Patent is hereby corrected as shown below:

In Claim 7, Col. 36, line 30, please change "carbon" to --carboxy--.

In Claim 8, Col. 37, line 30, please change "carboxyethyl" to --carboxymethyl--.

In Claim 8, Col. 37, line 39, please change "aria" in each instance to --and--.

Signed and Sealed this

First Day of September, 1998

BRUCE LEHMAN

Attest:

Attesting Officer

*Commissioner of Patents and Trademarks*